United States Patent [19]

Kakutani et al.

[11] Patent Number: 4,988,624
[45] Date of Patent: Jan. 29, 1991

[54] LYMPHOTOXIN DNA, LYMPHOTOXIN EXPRESSION VECTOR

[75] Inventors: Tetsu Kakutani; Kenji Yamashita, both of Kakogawa; yasuhiro Ikenaka, Akashi; Hajime Kawaharada, Kakogawa; Kiyoshi Watanabe, Akashi, all of Japan

[73] Assignee: Kanegafuchi Kagaku Kogyo Kabushiki Kaisha, Osaka, Japan

[21] Appl. No.: 882,109

[22] Filed: Jul. 3, 1986

[51] Int. Cl.$^5$ .................. C12N 15/00; C12N 15/19; C12N 15/63; C12N 15/67
[52] U.S. Cl. .................................. 435/320.1; 536/27; 435/172.3; 935/36; 935/27
[58] Field of Search .................. 435/68, 172.3, 240.2, 435/41; 530/350, 395; 935/34, 70

[56] References Cited

U.S. PATENT DOCUMENTS 4,727,028  2/1988  Santerre et al. .................. 435/240.2
4,740,461  4/1988  Kaufman .............................. 435/68

FOREIGN PATENT DOCUMENTS 0164965  12/1985  European Pat. Off. .

OTHER PUBLICATIONS

Wickner, in The Molecular Biology of the Yeast Saccharomyces CSH, 1981, pp. 415–439.
Cloning and Expression of cDNA for Human Lymphotoxin, a Lymphokine with Tumor Necrosis Activity, Gray et al., Nature, vol. 312 20/27 Dec., 1984, pp. 721–724.

Primary Examiner—Richard A. Schwartz
Assistant Examiner—S. L. Nolan
Attorney, Agent, or Firm—Armstrong, Nikaido Marmelstein, Kubovcik & Murray

[57] ABSTRACT

A chromosomal DNA sequence which codes for human lymphotoxin, a lymphotoxin expression vector which contains a DNA sequence wherein a chromosomal DNA sequence coding for human lymphotoxin and promoter region which functions in animal cell are linked together, lymphotoxin resistant cell line, transformed animal cell culture which is formed by transforming cultured animal cell with a lymphotoxin expression vector which contains a chromosomal DNA sequence coding for human lymphotoxin and, a process for preparing human lymphotoxin, which comprises transforming cultured animal cell with a lymphotoxin expression vector which contains a chromosomal DNA sequence coding for human lymphotoxin, culturing the transformed cell culture to produce human lymphotoxin, and collecting the human lymphotoxin.

According to the present invention, LT which is expected for application as the antitumor agent can be produced effectively in a large amount.

7 Claims, 15 Drawing Sheets

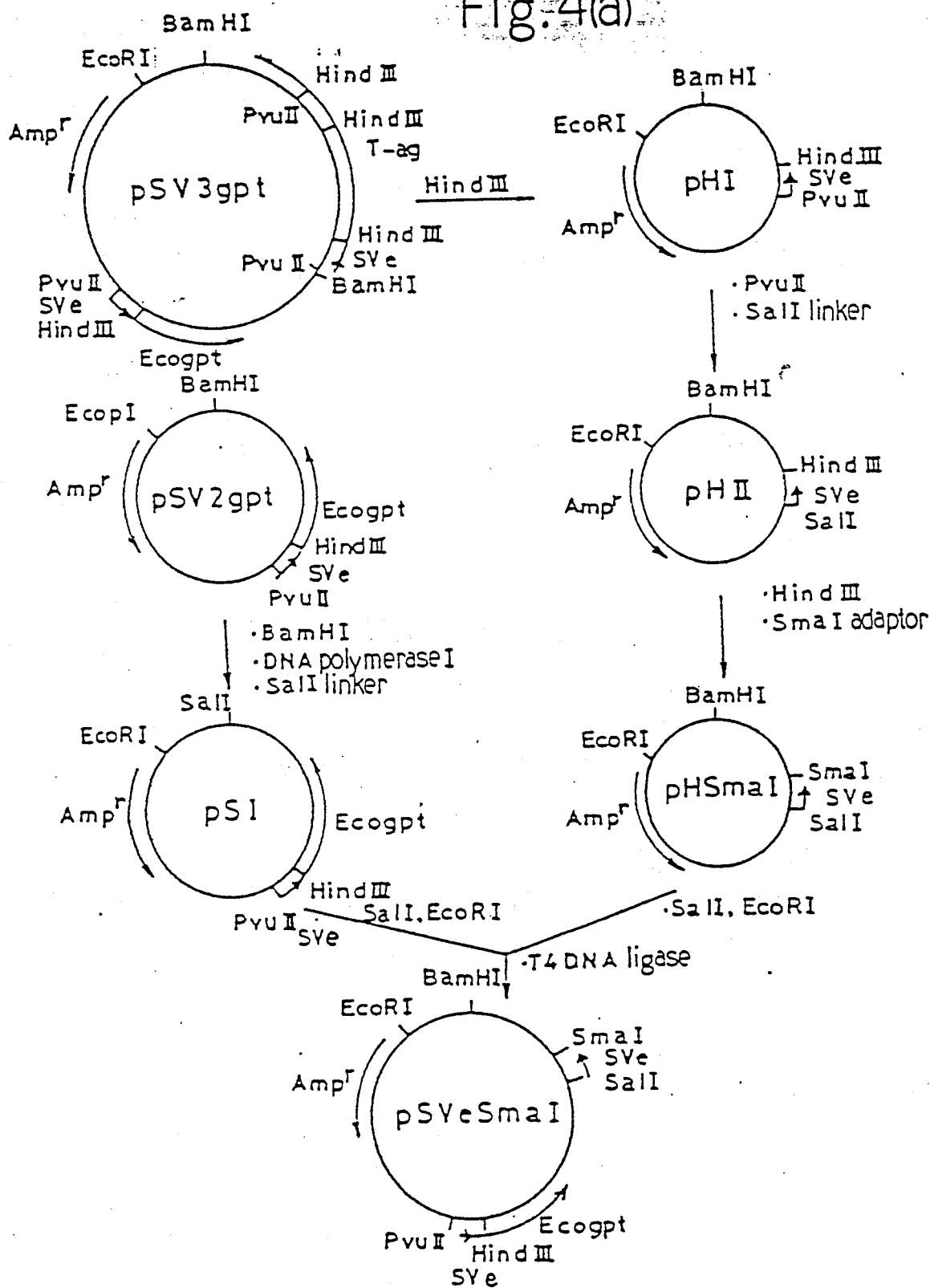

BamHI digestion     BamHI digestion

T4 DNA ligase

LYMPHOTOXIN DNA, LYMPHOTOXIN EXPRESSION VECTOR

BACKGROUND OF THE INVENTION

The present invention relates to a chromosomal DNA sequence which codes for human lymphotoxin, a lymphotoxin expression vector, a lymphotoxin resistant cell line, a lymphotoxin resistant cell line transformed with the lymphotoxin expression vector, and a process for preparing lymphotoxin by employing the lymphotoxin resistant cell line or the lymphotoxin resistant mutant cell line transformed with the lymphotoxin expression vector.

Lymphotoxin (hereinafter referred to as "LT") has a toxicity selective to cancer cell and capable of leading the cancer cell to necrosis [Evans, C. H. et al. (1977), Cancer Res., Vol. 37, P898]. LT, which is expected for application as the antitumor agent, is a kind of lymphokine induced by stimulating lymphocyte from animal such as man or mouse with lectins such as phytohemagglutinin and concanavalin A or with phorbol ester [Devlin, J. J. (1984), Lymphokines, Vol. 9, P313]. As the representative LT producing cell in man, T cell which is selected by rosette formation with sheep red cell or B cell RPMI 1788 is known [Aggarwal, B. B. et al. (1984), J. Biol. Chem., Vol. 259, P686]. LT is a kind of glycoprotein [Toth, M. K. and Granger, G. A. (1979), Mol. Immunol., Vol. 16, P671] and has several kinds of molecular forms. LT has been studied from protein chemical aspects by several research groups. It has been reported that LT is constructed from a minimum unit having a molecular weight of about 20000, which associates with each other or forms a complex with other components [Aggarwal, B. B. et al. (1984), J. Biol. Chem., Vol. 259, P686].

It is known that LT is produced by the lymphocyte stimulated with phorbol ester, mitogen or the like. However, in this process, only extremely small quantities of LT is produced and a large amount of fresh lymphocyte is required, which make the process unsuitable for a large-scale production of LT. It is also known that LT is produced inductively by stimulating the established cell derived from lymphocyte (established cell line) with mitogen or the like. However, productivity of LT in this process varies depending on the ability of the cell employed and thus the process is not suited for a large-scale production. In recent years, cDNA of LT has been cloned and it has become possible to produce LT-like protein in E. coli [Gray, P. W. et al. (1984), Nature, Vol. 312, P721]. However, in most cases, LT-like protein produced in microorganism has a N-terminal different from that of the natural one, since the microorganism has a protein synthetic mechanism which is somewhat different from that of the animal cell. Further, LT-like protein produced in a microorganism does not contain a sugar moiety linked to the protein whereas natural LT does.

A structure of LT sugar moiety remains mostly unknown. It is not known whether there is a difference in structure and antigenicity between LT produced by the human cell and LT produced by the non-human cell. However, LT produced by a human cell is supposed to closely resemble the natural LT and to have more safety than LT produced by the non-human cell. When LT is produced by the non-human cell, there is a possibility of contamination of LT product with constructive materials such as proteins or secretions from cells other than human cells and thus one can expect problems such as allergic reaction or shock when the LT product is administered in a long term as a therapeutic agent. On the other hand, LT product produced by the human cell contains only human material and does not contain any material other than that present in human blood, which improves the safety of the product.

From the above point of view, a process for preparing natural LT having the sugar moiety have been investigated.

In recombinant DNA technique, various problems are raised.

It is known that many proteins in higher organisms are coded on the chromosomal DNA sequence in several separated portions DNA sequence which codes matured mRNA is referred to as the "exon" while the separating sequence is referred to as the "intervening sequence" or "intron". Although the biological roles or functions of the introns remains still almost unknown, it is known that a gene without the intron such as those coding ovalbumin [Wickens, M. P. et al. (1980), Nature, Vol. 285, P628] or viral protein [Lai, C-J. et al. (1979), Proc. Natl. Acad. Sci. USA, Vol. 76, P71] produces far less protein in the animal cell as compared with the intron containing gene. It is also known that accumulation of stable mRNA occurs when the intron from β-globin gene is added to SV40 gene devoid of the intron [Hamer, D. H. et al. (1979), Cell, Vol. 18, P1299].

Removal of the sequence corresponding to the intron from nascent mRNA, which is transcribed from gene, is referred to as the "splicing". The splicing is presumed to be necessary for accumulation of stable mRNA or for transfer of mRNA from nucleus to cytoplasm.

For the expression of normal and functional protein, it is indispensable that the splicing occurs at the correct position. It has been reported that the abnormal splicing was observed when the insulin gene is linked with the promoter region of SV40, which is then introduced into COS cell [Laub, 0. et al. (1983), J. Biol. Chem., Vol. 258, P6043]. It is also known that the expression of amylase gene is conducted through tissue specific splicing, wherein salivary gland amylase and liver amylase are synthesized by way of two different splicing process from one and the same gene [Young, R. A. et al. (1981), Cell, Vol. 23, P451]. Also in SV 40 [Berk, A. J. et al. (1978), Proc. Natl Acad Sci. USA, Vol. 75, P1274], adenovirus [Chow, L. T. (1977), Cell, Vol. 12, Pl] and the like, more than one mRNA and protein are synthesized through different splicings from one and the same gene.

Therefore, the correct splicing is required in order to produce LT by introducing LT gene with the intron into the cultured animal cell. The present inventors have found that normal splicing occurs to secrete LT into the culture medium when LT coding chromosomal DNA sequence is linked with DNA sequence of the promoter region which functions in the cultured animal cell and initiates mRNA synthesis, which is then introduced into the various cultured animal cells.

For the production of LT which has the same amino terminal as that of natural LT and has the sugar moiety, gene recombination technique can be applied where the cultured animal cell is employed as the host. In this case, the introduction of only LT gene into the cultured animal cell is presumed not to lead to LT production. That is, LT is an inducible protein and the expression of LT gene is suppressed at the genetic level. In fact, the present inventors found that the amount of produced LT was quite small even if LT gene, which included the expression controlling region such as promoter, was introduced into various cultured cells. This suggests that some improvement must be made on LT gene in order that the cell wherein LT gene is introduced has the effective productivity of LT. The abovementioned improvement on LT gene is one of the main purposes of the present invention.

In 1981, Banerji et al. showed that the expression of rabbit β-globin gene is enhanced by the 72 bp repeat present in the vicinity of replication origin of SV40 DNA closely linked to the β-globin gene [Benerji, J. et al. (1981), Cell, Vol. 27, P299]. The enhancing effect of the 72 bp repeat in SV40 was observed at every position and direction of the linked sequence. Such relatively short DNA sequence which enhances the gene expression is referred to as the enhancer sequence. It was found that the enhancer sequence is also present in the genom of Rous sarcoma virus (RSV), polyoma virus, bovine papilloma virus and the like [Gluzman, Y. and Shenk, T. ed., Current communications in molecular biology, Cold Spring Harbor Laboratory (1983)]. It is also known that the enhancer is present in the intron of immunoglobulin gene [ibid].

The expression vector of LT utilizing such enhancer sequence is characterized by that it reduces the possibility of abnormal splicing and of the production of abnormal protein since the original promoter of LT gene functions.

On the other hand, it appeared difficult to obtain the subculturable cell line transformed with the LT expression vector since LT is strongly toxic to the cell and thus the cell transformed with the LT expression vector will be killed by the self-produced LT. However, the present inventors have found that the transformed BHK cell, wherein the LT expression vector is introduced, can produce LT, the transformed BHK cell being subculturable to produce LT for a long period of time. The present inventors have tested the susceptibiliy of BHK cell to LT and have found that the BHK cell is resistant to LT. On the other hand, the cells such as some CHO line, FL and WISH were sensitive to LT and died. When these LT-sensitive cells were transformed with the LT expression vector, the resultant transformed cells showed no production of LT or production of only a very small amount of LT. Vero and WI-26 VA4 cells, which are resistant to LT like BHK cell, gave the transformed cell line which stably produced LT.

Hitherto, a large number of the cell has been established. Among them, some established cell line while showing sensitivity to LT has excellent characteristics for cell breeding such as high efficiency of transformation, facility in obtaining the transformed cell line, low serum-dependency in cell growth, rapid growth, facility in a large-scale culture, high ability of synthesizing or secreting the protein having well-known properties of the cell and having specific genetic property. Therefore, also in these established cells, it is very important for the production of LT to establish the technique to obtain the transformed cell line which stably produces a large amount of LT.

The present inventors have established the technique to separate the LT resistant cell, from which the transformed cell line being obtained to produce LT stably. These cells could produce LT also in the serum free medium. The employment of the serum free medium in the LT production not only faclitates recovery and purification of LT from the medium but also prevents contamination of the products with serum component.

When the gene is introduced into the cell, the gene is sometimes incorporated into the host chromosomal DNA stably. The incorporated position of the gene in the chromosome is apparently random and a copy number of the incorporated DNA is also irregular. When LT gene is introduced into the cell, the incorporated position and the copy number vary in every cell, each cell producing a different amount of LT. Therefore, the cells which produce various amount of LT can be obtained by cloning the cell. The amount of the produced LT is presumed to have correlation with the copy number of LT gene and the cell having the increased number of LT gene is expected to show the improved productivity of LT.

SUMMARY OF THE INVENTION

In accordance with the present invention, there are provided a chromosomal DNA sequence which codes human lymphotoxin, lymphotoxin expression vector, lymphotoxin resistant cell, animal cultured cell transformed with the lymphotoxin expression vector and a process for preparing human lymphotoxin by employing the animal cultured cell transformed with the lymphotoxin expression vector.

BRIEF DESCRIPTION OF THE DRAWINGS

FIG. 4(a) Shows construction of plasmid pSVeSmaI.

FIG. 9(b) shows construction of plasmid pSVLpTKLT.

In FIG. 1, E-I, E-II, E-II and E-IV show 1st exon, 2nd exon, 3rd exon and 4th exon of LT gene, respectively.

In FIGS. 2 to 14, Amp$^r$, dhfr, Ecogpt, LT or HuLT, TK, CAT, T-ag, SVe, pA, pTA and e show ampicillin resistant gene, dhfr gene, guaninephosphoribosyltransferase gene of E. coli, LT gene, thymidine kinase gene of herpes simplex virus, chloramphenicol acetyltransferase gene, T-antigene of SV40, early promoter region of SV40, region including polyadenylation signal of SV40, promoter region of thymidine kinase gene of herpes simplex virus and enhancer region of Rous sarcoma virus, respectively.

DETAILED DESCRIPTION (1) Cloning of LT gene

Figure 1:
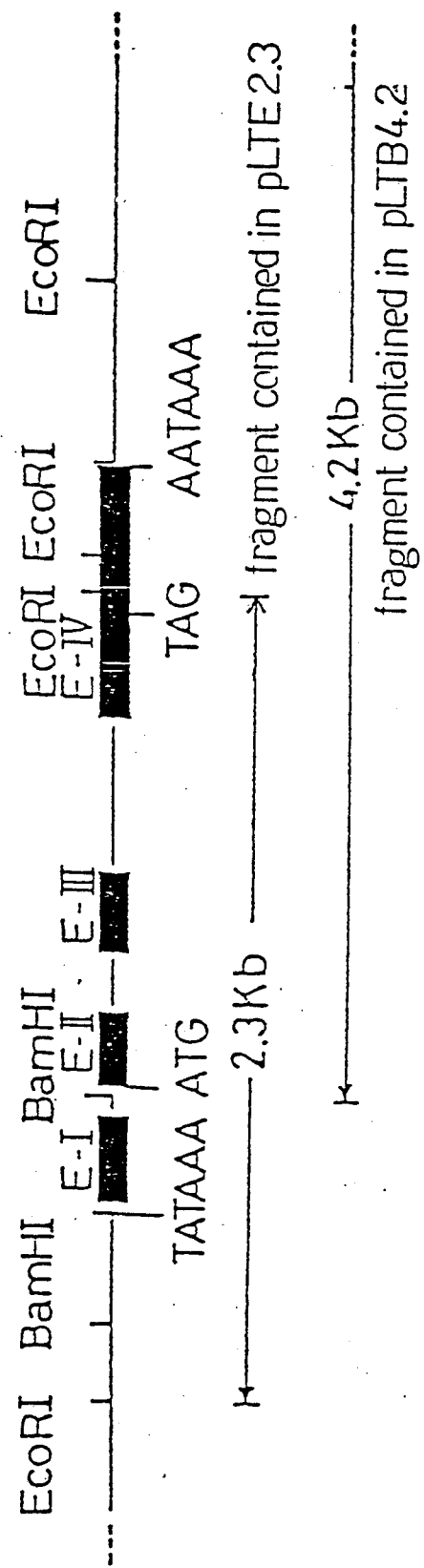
FIG. 1 shows chromosomal DNA fragment containing human LT gene.
Figure 2:
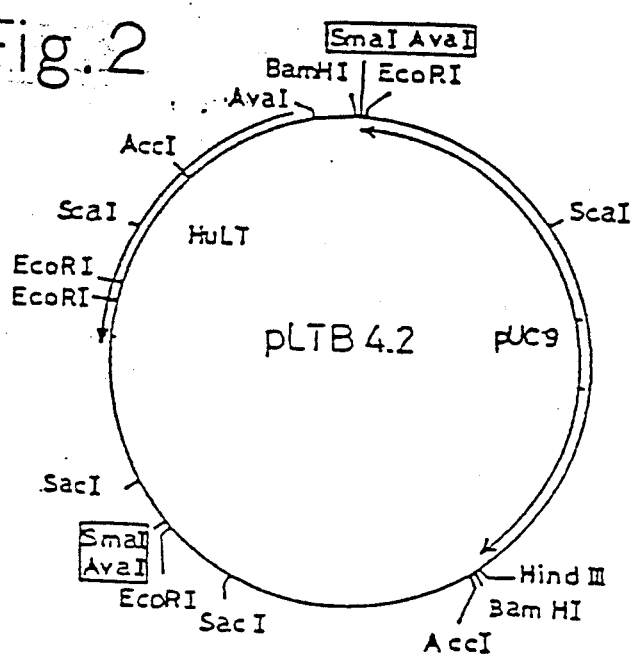
FIG. 2 shows plasmid pLTB 4.2.

The LT-coding chromosomal gene region was confirmed by the cloning and analytical study of the present inventors. The region has the restriction enzyme recognition sites as shown in FIG. 1. The LT-coding gene is the DNA sequence which includes the LT coding region, i.e. from codon ATG for methionine, which is the initiating amino acid in protein synthesis, to the termination condon TAG. The gene is, for example, included in BamHI 4.2 Kb in plasmid pLTB 4.2 as shown in FIG. 2. LT gene including the promoter region is the gene region at least from the control region including TATA box to the 4th exon as shown in FIG. 1.

The LT-coding chromosomal DNA sequence is cloned from human DNA. The human DNA is prepared according to Blin et al. [Blin, N. et al. (1976), Nucleic Acids Res., Vol. 3, P2303] employing, for example, cultured cell of human leucocyte or tissue. For the cloning of the LT gene, $\lambda$ phage vector such as Charon 28, plasmid vector such as pBR 322, cosmid such as pHC 79 and the like are employed Generally, gene manipulation technique with $\lambda$ phage, which is capable of cloning long-chain DNA in high frequency, is employed. After digesting human macromolecular DNA with proper restriction enzyme, the obtained fragment is inserted into the substitutable region of $\lambda$ phage DNA to form recombinant phage DNA. Then infectious phage particle is prepared by the in vitro packaging technique. The phage particle is then inoculated on the plate together with the host E. coli to form the recombinant phage plaque [Enquist, L. et al. (1979), Methods in Enzymology, Vol. 68, P281; Horn, B. (1979), Methods in Enzymology, Vol. 68, P299]. For detecting the recombinant phage plaque containing LT-coding DNA fragment, plaque hybridization technique [Woo, S.L.C. (1979), Methods in Enzymology, Vol. 68, P389; Szostak, J. W. et al. (1979), Methods in Enzymology, Vol 68, P419] is employed with cDNA or synthesized DNA as a probe. Further, the recombinant phage containing LT gene is collected from the plaque selected by the plaque hybridization technique and is prepared in a large amount by cultivation with the host E. coli. DNA of the recombinant phage is prepared by phenol extraction method and the like [Maniatis, T. et al. (1982), Molecular Cloning a Laboratory manual, Cold Spring Harbor Laboratory].

The amino acid sequence of LT can be estimated from the base sequence of the exon portion of the cloned LT gene. The base sequence is determined by the Maxam-Gilbert method [Maxam, A. M. et al. (1980), Methods in Enzymology, Vol 65, P499], the dideoxy method by Sanger [Sanger, F. (1981), Science, Vol. 214, P1205] or the like.

(2) LT expression vector

LT is an inducible protein and is induced by stimulating human leucocyte with some mitogens and the like. Though at present it is not known how the stimulation with mitogen works on the LT gene to induce LT, it will follow that the introduction of the LT gene containing the control region into the cell which is not endowed with such induction mechanism produces only slight amount of LT. The present inventors have found that the cell which does not produce LT can be transformed into the cell which produces LT in a large amount by linking the other gene promoter region, which functions in the cultured animal cell, to the 5' site of the LT-coding chromosomal DNA sequence In this case, mRNA synthesis of LT is under the control of the linked promoter region. If the linked promoter region is derived from the gene for the constitutive protein, mRNA of LT is synthesized in the cell at all times and thus the cell becomes the cell which constitutively produces LT. If the linked promoter region is derived from the gene for the inducible protein, the transformed cell produces LT as the inducible protein.

As the promoter which functions in the cultured animal cell, the early gene promoter of SV40 is known. This promoter is contained in the Hind III-PvuII fragment of SV40 DNA 350 bp in size. The DNA fragment also functions as the late gene promoter in reverse direction. Transcription activity from the late gene promoter of SV40 is generally enhanced in the presence of T-antigen of SV40. Therefore, for the cell wherein LT gene linked to the late gene promoter is introduced, the cell which can express T-antigen gene is preferably employed. The cell wherein T-antigen gene is expressed can be prepared by introducing T-antigen-coding gene into the cell. When the cultured cell is transformed with DNA sequence wherein LT gene linked to T-antigen DNA sequence of SV40 and to the late promoter of SV40 is present on one and the same sequence, the cell line which shows high LT expression will be obtained in many kinds of the established cell.

Thymidine kinase promoter of herpes simplex virus (HSV) type I is the constitutive promoter like the early gene promoter of SV40, the structure thereof being shown by Wagner et al. [Wagner, M. J. et al. (1981), Proc. Natl. Acad Sci. USA, Vol. 79, P1441]. The functioning promoter region is referred to as the promoter region which contains the mRNA initiation site but not the codon for methionine, the first amino acid of the protein which is regulated by the promoter. Preparation of DNA sequence (LT expression vector) is shown in the Example as described below, wherein the functional promoter region and the chromosomal DNA sequence of LT are linked together.

In order that only the cell wherein the desired gene is introduced and the stable expression is observed may grow, it is preferable to employ DNA sequence wherein the linked sequence of the functional promoter and LT gene and selectable marker gene are present on one and the same DNA sequence For the selectable marker gene in the animal cell, genes such as Ecogpt [Mulligan, R. C. et al. (1980), Science, Vol 209, P1422], neo [Southern, P. J. et al. (1982), J. Mol. Appl. Genet., Vol. 1, P327] or dhfr [Wigler, M. et al. (1980), Proc. Natl. Acad. Sci. USA, Vol. 77, P3567] are employed. For preparing such DNA sequence in a large amount, such DNA sequence is preferably a replicon such as plasmid or phage DNA which is capable of replicating in E. coli and of being prepared in a large amount. The LT expression vector shown in the Example is the plasmid fit for the above-mentioned purpose; the plasmid characterized by that DNA replication origin (ori) which enables replication in E. coli and chromosomal DNA sequence of LT, to which selectable marker gene (ampicillin resistant gene), selectable marker gene in the cultured animal cell (Ecogpt) and the functioning promoter are linked, are present on one and the same DNA sequence.

The present inventors have prepared the LT expression vector which contains dhfr. The cell line transformed with the LT expression vector having dhfr can be easily selected in the medium without nucleosides when dhfr− established cell line is employed as the host. dhfr gene such as pSV2dhfr [Mulligan, R. C. and Berg, P. (1980), Science, Vol. 209, P1422] or pAdD26SV(A) [Kaufman, R. J. and Sharp, P. A. (1982), Molecular and Cellular Biology, Vol. 2, P1304] can be employed. The dhfr gene from the micoorganism can also be employed as well as that from the higher animal. As the established cell line defective of dihydrofolate reductase enzyme (dhfr−), CHO dhfr− [Urlaub, G. and Chasin, L. (1980), Proc. Natl. Acad. Sci. USA, Vol. 77, P4216] is known.

LT-coding DNA sequence in the LT expression vector having dhfr gene may be the chromosomal DNA sequence of LT, cDNA sequence or synthesized DNA sequence, which is capable of LT expression. Also DNA sequence, part of which is artificially modified, or DNA sequence which has mutation such as deletion, substitution, insertion or translocation can be employed.

Even though the gene containing the promoter region was introduced into the cell, the production of LT was quite low. This shows that the LT promoter is in a passive state which does not synthesize mRNA efficiently in the cell wherein LT is not produced. The present inventors have constructed the LT expression vector while utilizing the enhancer sequence in order to activate the LT promoter. Although it is known that the enhancer shows cellular specificity, any enhancer can be employed which can activate the LT promoter in the host cell. For example, 72 bp repeat of SV40, the enhancer of polyoma virus, the enhancer of bovine papilloma virus, the enhancer of adenovirus, the enhancer of Rous sarcoma virus, the enhancer of immunoglobulin and the like can be employed. The enhancer can be inserted at any position or orientation if it can activate the LT promoter and does not inhibit the matured mRNA synthesis of LT. A number and a kind of the incorporated enhancer are also not restricted as far as the enhancer can activate the LT promoter. Plasmid pLT-R3 described in the Example is the LT expression vector which has three enhancer sequences of Rous sarcoma virus in positive direction about 800 bp upstream from TATA box of the LT gene toward the 5' site.

An amount of LT produced by the LT resistant cell transformed with the LT expression vector has a correlation with a copy number of LT gene contained in the transformed cell. The cell which had higher copy number of the LT gene and thus had higher productivity of LT could be separated, after the LT expression vector having the amplifiable gene was introduced into the cell, by a single cell separation or by selecting the cell in the condition wherein only the cell in which the amplifiable gene is amplified can selectively grow. As the amplifiable gene, dihydrofolate reductase gene, aspartate transcarbamylase gene and metallothioneine gene can be employed. Other amplifiable gene [Stark, G. R. and Wahl, G. M. (1984), Annu. Rev. Biochem., Vol. 53, P447] can also be employed From the cell transformed with the LT expression vector containing dihydrofolate reductase gene, the cell wherein the dihydrofolate reductase gene is amplified can be selected, after transformation, in the medium containing not less than 1 nM of methotrexate. In many cases, not only dihydrofolate reductase gene but also LT gene are amplified in the selected cell. Similarly, the cell having the amplified gene can be selected by a heavy metal in case of the metallothioneine gene and by N-(phosphonacetyl)-L-aspartate (PALA) in case of the aspartate transcarbamylase gene As the host cell wherein the LT expression vector having the amplifiable gene is introduced for producing LT at some requested concentration, any cell can be employed which shows resistance to LT at not less than the above concentration. When the dihydrofolate reductase gene (dhfr) is employed as the amplifiable gene, the established dhfr− cell is preferably employed since the established cell having the amplified gene can be easily separated by methotrexate.

The cell having the same property as the LT-resistant cell transformed with the LT expression vector having the amplifiable gene can also be obtained by the co-transfection, i.e. transformation with DNA containing the amplifiable gene and with the LT expression vector. LT gene in the cell obtained by the co-transfection is presumed to be amplified together with the amplifiable gene, which is also within the scope of the present invention.

(3) Selection of the LT-resistant established cell

In order to introduce the LT expression vector into the cell to produce LT at some desired concentration, the host cell is required to be resistant to LT at least at the desired concentration. Since in practice a concentration of LT around the LT-secreting cell is presumed to be higher than the other circumstances, the host cell will be required to be resistant to LT at more than the desired concentration. For confirming whether the cell shows the resistance to LT at the fixed concentration, the cell is subcultured in the medium containing LT at that concentration. The LT sensitive cell is lowered in its growth rate during the cultivation due to toxicity of LT, is degenerated, deformed or finally dies whereas the LT resistant cell grows continuously and thus the LT resistant cell can be easily selected. When actynomycin D or mitomycn C is present in the medium, a sensitivity of the LT sensitive cell is increased and degeneration and deformation are accelerated, which distinguishes the LT sensitive cell from the LT resistant cell.

From the cell sensitive to LT at some concentration, the cell resistant to LT at not less than the concentration can be obtained by subculturing the cell in the medium containing LT at not less than the concentration. The cell sensitive to LT at the concentration is lowered in its growth rate during the cultivation, is degenerated, deformed or finally dies whereas the cell which acquired the resistance continues to grow and can be easily isolated. In this case, the cell may be treated previously with the mutagenic agent such as ethylmethane sulfonate before selection with the medium containing LT. Further, sensitivity of the LT sensitive cell is increased and degeneration and deformation are accelerated when actinomycin D or mitomycin C is present in the medium, which allows the concentration of the cell which acquired the LT resistance in a short period of time. The cell which acquired the LT resistance is referred to as the "LT resistant mutant cell" in the present invention. The LT resistant mutant cell is included in the cell showing the LT resistance, i.e. the LT resistant cell.

By the method as mentioned above, the LT resistant cell can be obtained from any sensitive cell as a rule.

LT resistant mutant cell is a cell that has acquired the LT resistance at higher concentration of LT than that of the mother cell but not necessarily accompanies the mutation in the gene of the cell.

In order that the cell can produce LT after the introduction of the LT expression vector, its DNA sequence is required to coincide with the specific function of the employed cell such as RNA synthesis system, maturation of RNA, protein synthesis system, maturation of protein or secretion of protein. After mRNA synthesis directed by the introduced DNA, processing of mRNA is required such as addition of the cap structure to the 5' terminal, splicing at the correct position and polyadenylation at the 3' terminal. For the production of active LT, formation and maintenance of the normal high-order structure of the synthesized LT polypeptide as well as release and secretion from the cell of the signal peptide must be correctly carried out. The present inventors employed the cultured animal cell derived from hamster, monkey or man which is available from American Type Culture Collection (ATCC). According to the process for preparing LT as described in the specification, active LT can be produced from the cultured cell, the fused cell, the normal or mutant cell, or the cell transformed with virus, which cells are derived from vertebrates. The employment of the established human cell which is trasformed with SV40 is expected to improve the safety of the product by taking a proper means, as compared with the cell transformed by a synthetic agent. As the cell transformed with SV40, WI-26 VA4 is known.

(4) Transformant of the LT resistant cell with the LT expression vector

In order to introduce the LT expression vector into the cell, potassium phosphate method [Wigler, M. et al. (1977), Cell, Vol 11, P223], microinjection [Anderson, W. F. et al. (1980), Proc. Natl. Acad. Sci. USA, Vol. 77, P5399], liposome method, DEAE-dextran method, cell fusion [Schoffner, W. et al. (1980), Proc. Natl. Acad. Sci. USA, Vol. 77, P2163] and the like are used. As DNA used in the potassium phosphate method, microorganism such as E coli or phage can also be employed as well as the DNA solution. In the cell fusion method, protoplasts of the microorganism containing the subject DNA sequence as a plasmid is employed.

After transformation by introducing the LT expression vector into the LT resistant cell, the subculturable cell which stably produces LT can be selected by the character given by the selectable marker gene which is either contained in the LT expression vector or introduced into the cell co-transfected with the LT expression vector. When the selectable marker gene is Ecogpt, the cell is selected as the mycophenolic acid resistant cell. When the selectable marker gene is dhfr, the cell can be easily separated as the nucleoside independent cell in the medium without nucleosides by employing the established LT resistant dihydrofolate reductase deficient cell, i.e. the established dhfr− *cell as the host. The established dhfr− cell can be prepared according to Urlaub et al.* [Urlaub, G. and Chasin, L. (1980), Proc. Natl. Acad. Sci. USA, Vol. 77, P4216].

From the transformant cell with the LT expression vector having dihydrofolate reductase gene, the cell having the amplified dihydrofolate reductase gene can be selected, after transformation, in the medium containing not less than 1 nM of methotrexate. In many cases, not only dihydrofolate reductase gene but also LT gene are amplified in the selected cell. Further, the present inventors could obtain the cell which can produce a large amount of LT from the population by the single cell isolation technique in the medium containing not less than 1 nM of methotrexate. Similarly, the cell having the amplified gene can be selected by a heavy metal in case of the metallothioneine gene and by N-(phosphonacetyl)-L-aspartate (PALA) in case of the aspartate transcarbamylase gene.

Further, it has also been found that the transformant LT-producing cell with the LT expression vector could produce LT in the chemically defined medium completely deficient in serum as well as in the medium containing serum which has been usually employed in the cell culture. The employment of the chemically defined medium in the LT production not only facilitates recovery and purification of LT from the medium but also prevents contamination of the products with serum component.

The present invention is more particularly explained by the following Examples. However, it should be understood that the present invention is not limited to the Examples and various changes and modifications can be made without departing from the scope and the spirit of the present invention.

The experiments of the present invention were carried out according to "recombinant DNA experiment guideline" set by the Prime Minister. Manipulation of phage, plasmid, DNA, various enzymes, E. coli and the like in the Examples was according to the following Reference.

(1) Tanpakushitsu Kakusan Koso, Vol. 26, No. 4 (1981), extra eddition, Idenshisosa (Kyoritsu Shyuppan)
(2) Idenshisosa Jikkenho, Yasuyuki Takagi ed. (1980) (Kodansha)
(3) Idenshisosa Manyuaru, Yasuyuki Takgi ed. (1982) (Kodansha)
(4) Molecular Cloning a Laboratory manual, T. Maniatis et al. ed. (1982), Cold Spring Harbor Laboratory
(5) Methods in Enzymology, Vol 65, L. Grossman et al. ed. (1980), Academic Press
(6) Methods in EnzYmology, Vol. 68, R. Wu ed. (1979), Academic Press

EXAMPLE 1

Cloning of LT gene

Blood was taken from healthy adults into a heparinized test tube. The blood was diluted two-fold with commercial phosphate buffer solution (PBS) (made by Flowlaboratory Co. Ltd.) and then put on ficolpack solution (made by Pharmacia Co., Ltd.), followed by centrifugation at 2000 r.p.m. for 30 minutes to separate the leucocyte layer, which was further washed with PBS twice 20 ml of 0.5 M EDTA-0.5 % sarcosyl solution and 2 mg of Protease K were added per $10^8$ cells and the mixture was incubated at 50° C. for 3 hours. Extraction with phenol was conducted two times and the water layer was dialyzed against 50 mM Tris-10 mM EDTA-10 ml sodium chloride (pH 8.0) over night. 100 μg/ml of RNaseA was added to the resultant. After treatment at 37° C. for 3 hours, extraction with phenol was conducted two times and the water layer was dialyzed against 50 ml Tris-10 mM EDTA to give macromolecular human a DNA. After partially digesting the obtained human, a DNA with Sau3AI DNA fragment from the digest of about 15 to 20 Kb was isolated by sucrose gradient centrifugation After digesting λ phage vector Charon 28 DNA with BamHI, the fraction containing the left fragment of Charon 28 and that containing the right fragment were collected by sucrose gradient centrifugation, both fractions being recovered by precipitation in ethanol.

After both right and left DNA fragments of Charon 28 vector and human Sau3AI fragment of 15 to 20 Kb were linked with T4DNA ligase, in vitro packaging was carried out according to Enquist and Sternberg [L. Enquist and N. Sternberg (1979), Methods in Enzymology, Vol. 68, P281] employing E. coli LE 392 as the host to form the plaque of recombinant phage. The recombinant phage clone containing LT gene was selected by plaque hybridization [Benton, W. D. Davis, R. W. (1977), Science, Vol. 196, P180]. For the probe, three oligonucleotides having the base sequence present in the LT gene, ATGACACCACCTGAACGT, TCTACTCCCAGGTGGTC and ACTGTCTTCTTTGGAGCC, which correspond to the amino acid residues 29-34, 75-80 and 163-168 of LT respectively [Gray, P. W. et al. (1984), Nature, Vol. 312, P721], were synthesized by phosphotriester method [Miyoshi K. et al. (1980), Nucleic Acids Res., Vol. 8, P5507] the 5'-OH being labelled with γ-$^{32}$P]ATP and T4 polynucleotide kinase.

Eleven phage clones, which can hybridize with all three synthetic DNA probes, were obtained from about $6 \times 10^5$ recombinant phage clones. One of the phage clones, 4-1 was digested with various restriction enzymes. Agarose electrophoresis was conducted and, after transfer to nitrocellulose filter, Southern hybridization [Southern, E. M. (1975), J. Mol. Biol., Vol. 98, P503] was conducted employing the above three synthetic DNA probes, which proved that BamHI 4.2 Kb, EcoRI 2.3 Kb and SmaI 2.7 Kb fragments hybridized with the above three probes and that DNA sequence which codes the amino acid sequence of LT was contained in these fragments. As the result of the restriction enzyme analysis of several phage clone DNAs, the restriction enzyme recognition sites of the chromosomal DNA sequence of LT and of the surrounding sequence were mapped as shown in FIG. 1.

EXAMPLE 2

Subcloning of LT gene

After digesting DNA of the phage clone 4-1 with the restriction enzyme BamHI, the obtained 4.2 Kb fragment was inserted into the BamHI site of the plasmid pUC9 [Vieira, J. and Messing, J. (1982), Gene, Vol. 19, P259] to prepare pLTB 4.2 as shown in FIG. 2.

Base sequence of pLTB 4.2 was determined by dideoxy method [Wallace, R. B. et al. (1981), Gene, Vol. 16, P21] employing the commercial primers CAG-GAAACAGCTAT GAC and AGTCACGACGTT-GTA (made by Takara Shuzo Co., Ltd.), and the oligomers ACCTTGGGAGGAAGAG, TCTACTC-CCAGGTGGTC and ACTGTCTTCTTTGGAGCC, which correspond to the amino acid residues 23-28, 75-80 and 163-168 respectively, as the primer.

As the result, it was proved that the 5' site of LT had the base sequence of:

```
GGATC CCCGGCCTGCCTGGGCCTGGG
CCTTG GTGGGT ...intron... CTGCAG GTT
CTCCC CATGACACCACCTGAACGT...
                MetThrProProGluArg...
``` and the 3' site of LT had the base sequence of:

GCCTACTCTCCCAAGGCCACCTCCTCCCCA
AlaTyrSerProLysAlaThrSerSerPro
90
CTCTACCTGGCCCATGAGGTCCAGCTCTTC
LeuTyrLeuAlaHisGluValGlnLeuPhe
100
TCCTCCCAGTACCCCTTCCATGTGCCTCTC
SerSerGlnTyrProPheHisValProLeu
110
CTCAGCTCCCAGAAGATGGTGTATCCAGGG
LeuSerSerGlnLysMetValTyrProGly
120

Figure 3:
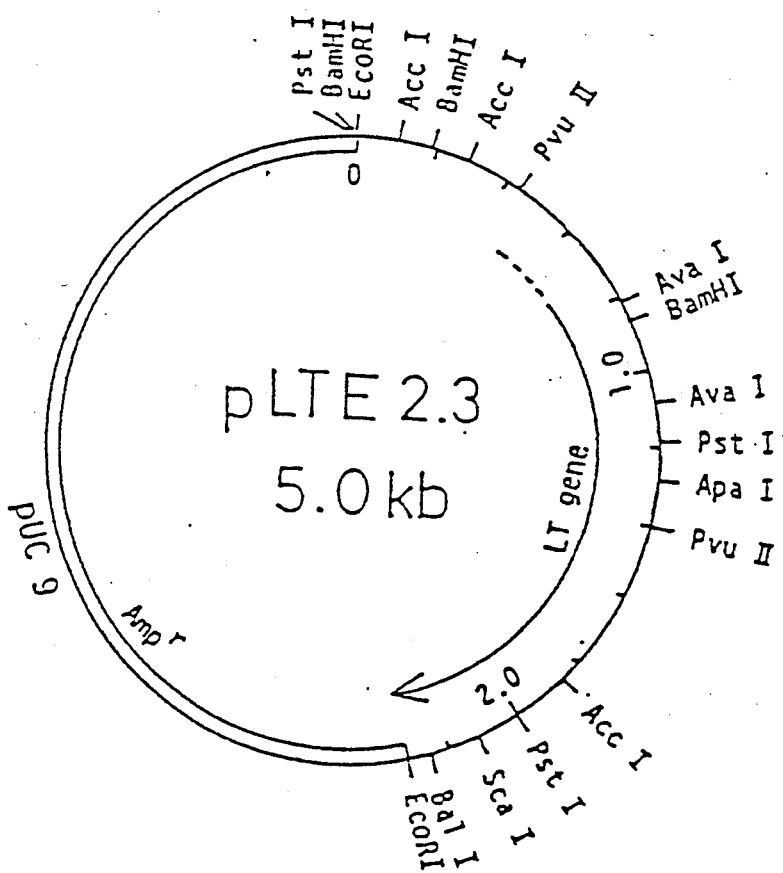
FIG. 3 shows plasmid pLTE 2.3.

-continued
CTGCAGGAACCCTGGCTGCACTCGATGTAC
LeuGlnGluProTrpLeuHisSerMetTyr
130
CACGGGGCTGCGTTCCAGCTCACCCAGGGA
HisGlyAlaAlaPheGlnLeuThrGlnGly
140
GACCAGCTATCCACCCACACAGATGGCATC
AspGlnLeuSerThrHisThrAspGlyIle
150
CCCCACCTAGTCCTCAGCCCTAGTACTGTC
ProHisLeuValLeuSerProSerThrVal
160
TTCTTTGGAGCCTTCGCTCTGTAGAACTTG
PhePheGlyAlaPheAlaLeu STOP
170
GAAAAATCCAGAAAGAAAAAATAATTGATT
TCAAGACCTTCTCCCCATTCTGCCTCCATT
CTGACCATTTCAGGGGTCGTCACCACCTCT
CCTTTGGCCATTCCAACAGCTCAAGTCTTC
CCTGATCAAGTCACCGGAGCTTTCAAAGAA
GGAATTCTAGGCATCCCAGGGGACCCACAC
TCCCTGAACCATCCCTGATGTCTGTCTGGC
TGAGGATTTCAAGCCTGCCTAGGAATTCCC
AG Although plasmid pLTB 4.2 contains entire DNA sequence which codes the amino acid sequence of LT, it does not contain the transcription initiating region which should be present upstream of the 5'site. Therefore, subsequently DNA of the phage clone 4-1 which contains LT gene was digested with the restriction enzyme EcoRI and the obtained 2.3 Kb fragment was inserted into the EcoRI site of the plasmid pUC9 to prepare pLTE 2.3. The structure of the plasmid pLTE 2.3 was shown in FIG. 3.

EXAMPLE 3

Preparation of pSVeSmaILT, pSVpTKLT, pSV2LLT and pSV3LLT

Figure 4B:
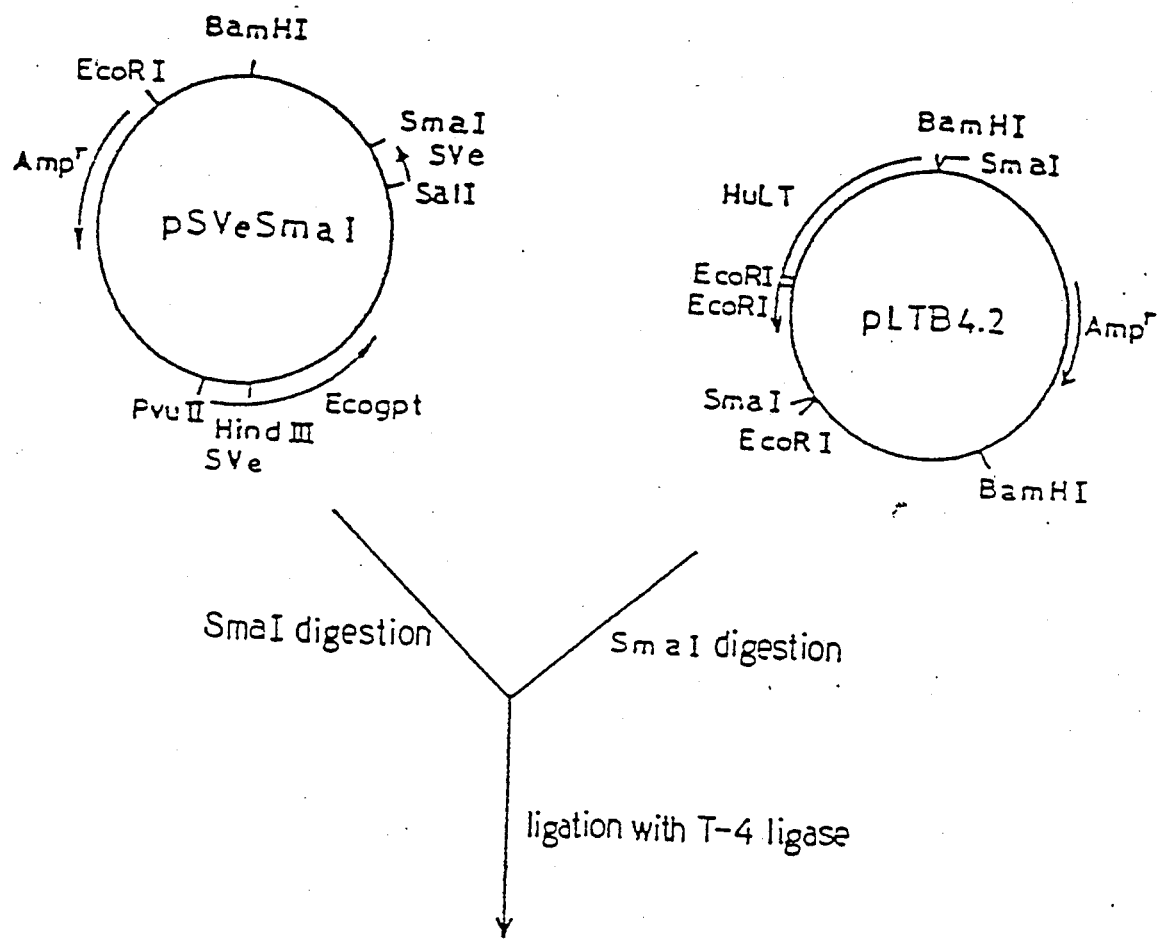
FIG. 4(b) shows construction of plasmid pSVeSmaILT.
Figure 4B:
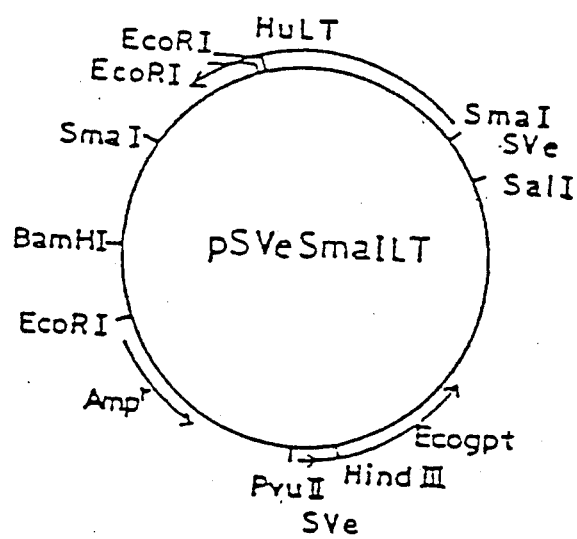

Starting from pLTB 4.2, pSV2gpt and pSV3gpt [Mulligan, R. C. and Berg, P. (1980), Science, Vol. 209, P1422], pSVeSmaILT plasmid, which has the sequence wherein the early gene promoter region of SV40 and the chromosomal DNA sequence of LT are linked, was prepared according to the procedure as shown in FIGS. 4(a) and 4(b).

Plasmid pSV3gpt was digested with HindIII and the obtained largest DNA fragment was cyclized with T4 DNA ligase to prepare pHI. PvuII site of pHI was then converted into SalI site by means of SalI linker to prepare pHII. Further, at the HindIII site of pHII was introduced SmaI site by means of HindIII-SmaI adaptor to prepare pHSmaI. BamHI site of pSV2gpt was cleaved with BamHI and the cleavage site was converted into the blunt end with DNa polymerase I (Klenow), which was then cyclized with T4 DNA lingase to prepare pSI. pHSmaI and pSI were cleaved with SalI and EcoRI and the resultant was linked with T4 DNA ligase to prepare pSVeSmaI. pLTB 4.2 was digested with SmaI to give the DNA fragment containing LT gene, which was then introduced into the SmaI cleavage site of pSVeSmaI to prepare pSVeSmaILT.

The employed SalI linker and SmaI adaptor had the sequence of d(pGGTCGACC) and d(pAGCTCCCGGG), respectively. As the DNA polymerase I, Klenow fragment was employed.

Figure 5:
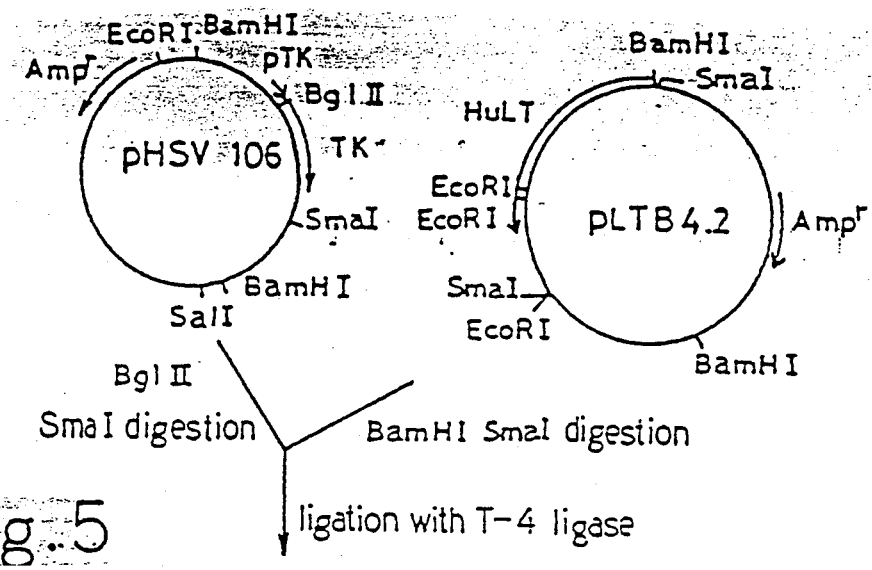
FIG. 5 shows construction of plasmid pSVpTKLT.
Figure 5:
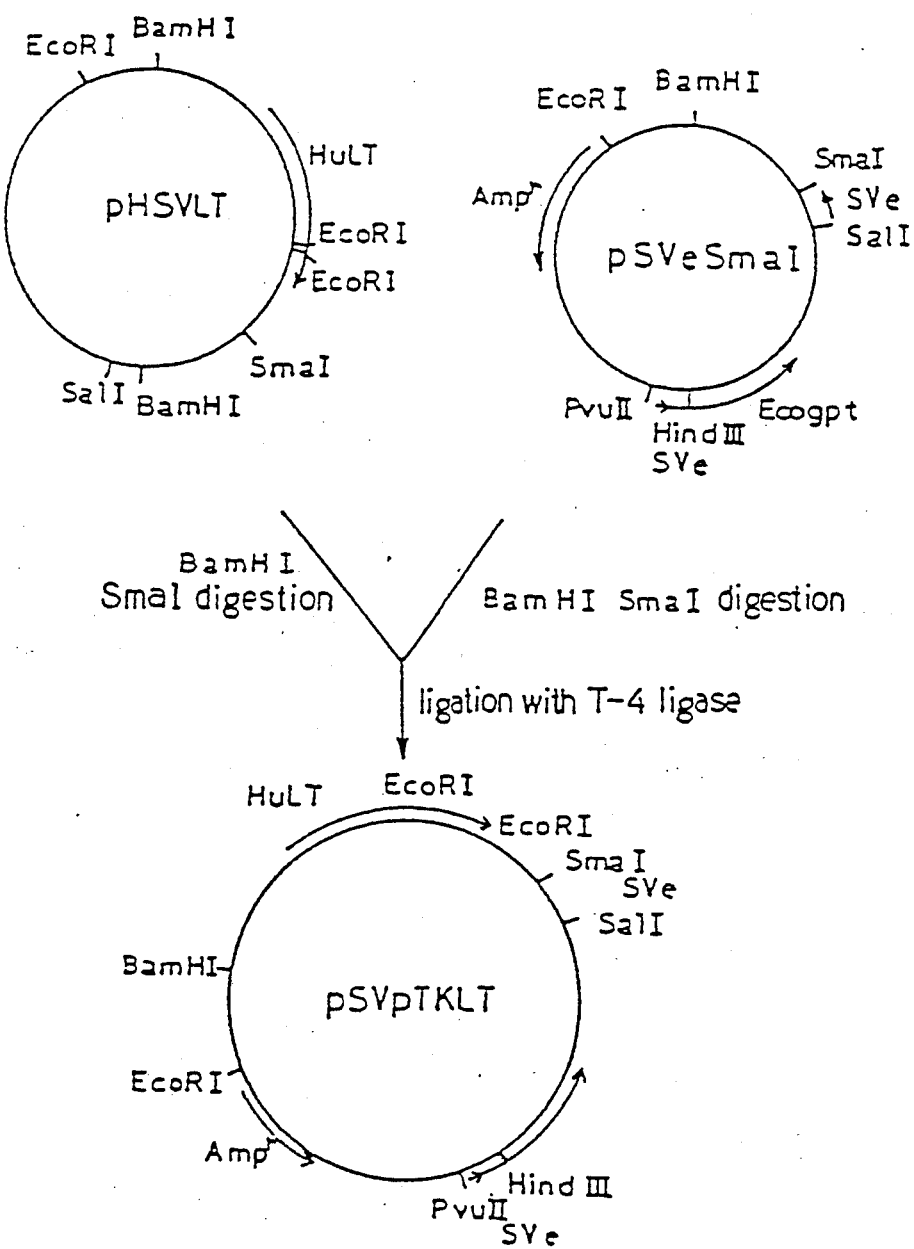

Plasmid pSTpTKLT, which has the sequence wherein the thymidine kinase promoter region of herpes simplex virus type I and LT gene are linked, was prepared starting from pLTB 4.2, pHSV 106 [Mc- Knight, S. L. and Gabis, E. R. (1980), Nucleic Acids Res., Vol. 8, P5931] and pSVeSmaI as shown in FIG. 5.

LT gene BamHI-SmaI fragment in pLTB 4.2 was inserted into the BglII-SmaI site of pHSV 106 to prepare pHSVLT. LT gene BamHI-SmaI fragment with the TK promoter in pHSVLT was introduced into the BamHI-SmaI site of pSVeSmaI to prepare pSVpTKLT.

Figure 6:
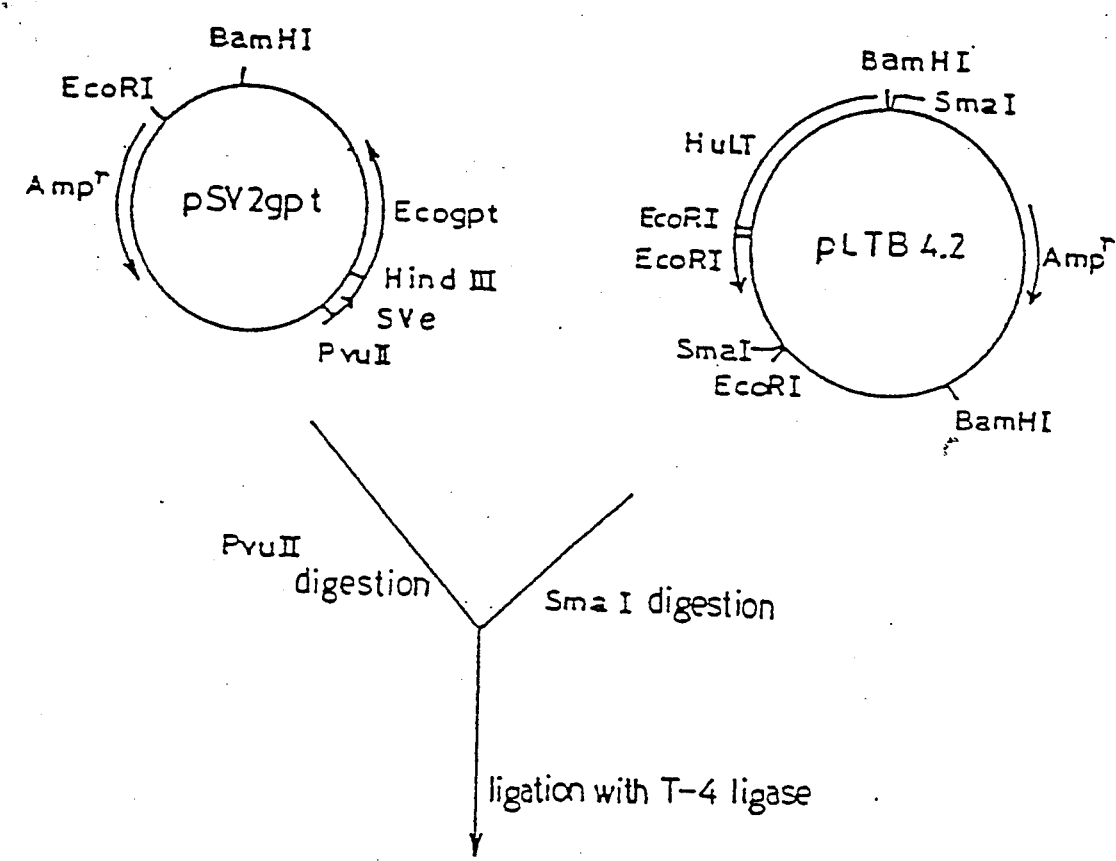
FIG. 6 shows construction of plasmid pSV2LLT.
Figure 6:
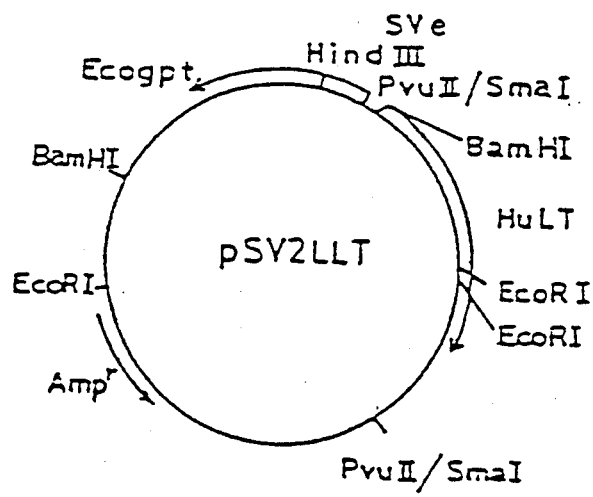
Figure 7:
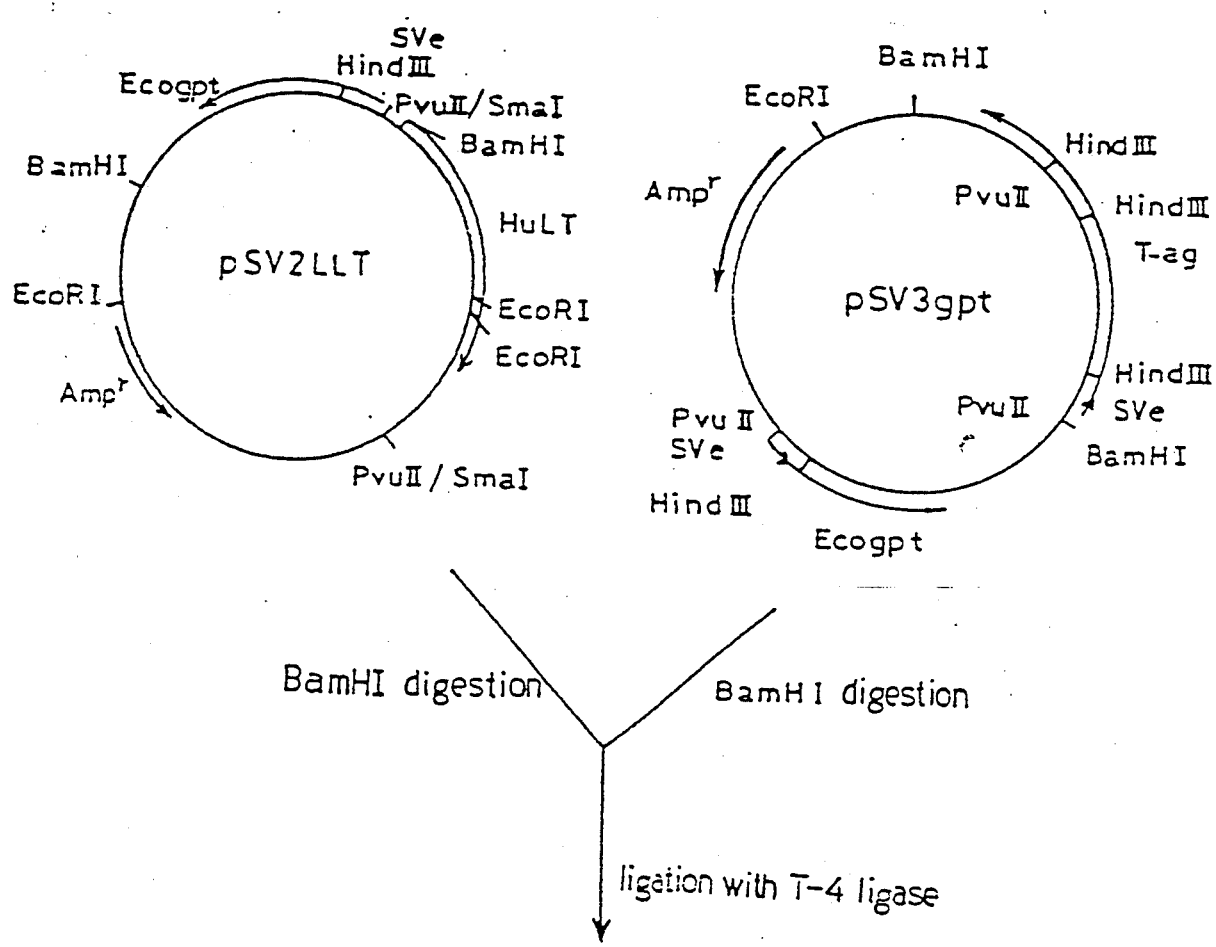
FIG. 7 shows construction of plasmid pSV3LLT.
Figure 7:
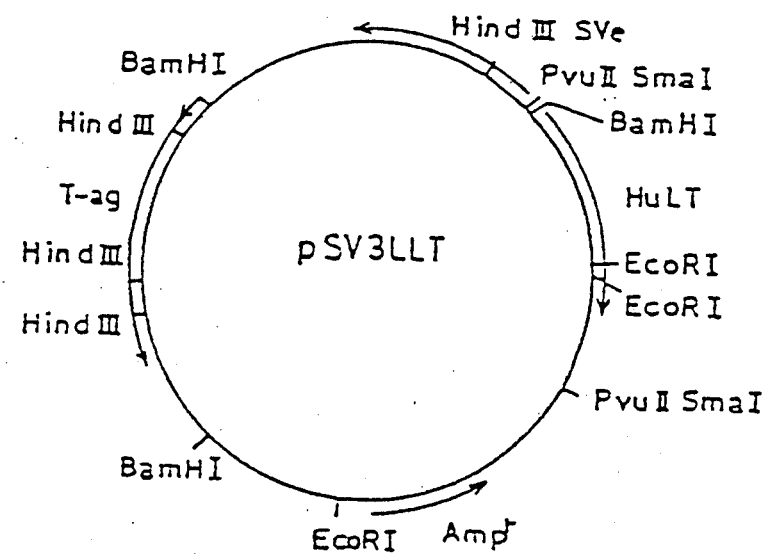

Plasmids pSV2LLT and pSV3LLT, which have the sequence wherein the late gene promoter region of SV40 and LT gene are linked, were prepared starting from pLTB 4.2, pSV2gpt and pSV3gpt as shown in FIGS. 6 and 7. LT gene SmaI-SmaI fragment of 2.5 Kb in pLTB 4.2 was linked to the PvuII site of pSV2gpt to prepare pSV2LLT. The obtained pSV2LLT was then partially digested with BamHI and to the cleavage site of BamHI was linked T-antigen gene BamHI fragment in pSV3gpt to prepare pSV3LLT.

EXAMPLE 4

Introduction of pSVeSmaILT, pSVpTKLT, pSV2LLT and pSV3LLT into the cultured cell and production of LT In order to examine the expression of LT gene contained in the expression vectors pSVeSmaILT, pSVpTKLT, pSV2LLT and pSV3LLT, the plasmids were introduced into the various cultured animal cells according to Wigler et al. [Wigler et al. (1977), Cell, Vol. 11, P223]. Coprecipitate of plasmid-calcium phosphate was added to the cell ($2 \times 10^5$ cells/3 ml medium/culture dish of 6 cm diameter) which was previously cultured on the Eagle's MEm medium containing 10% fetal calf serum. Amount of LT contained in the medium after 48 hours, while renewing the medium after 15 hours, was measured by the cellular lethal effect of LT employing L 929 cell as the target cell [Ruff, M. R. and Gifford, G. E. (1981), Lymphokines, Vol. 2, P235], i.e. the cell was cultured in 96-well multidish at $2 \times 10^4$ cells/well/100 μl medium for a day, to which, after the culture medium was removed, 100 μl of samples diluted to various concentrations with Eagle's MEM medium containing 1 μg/ml of Actinomycin D and 5% fetal calf serum were added. After 20 hours, cellular degeneration and lethel effect of LT was measured. As shown in Table 1, all cultured cells to which pSVeSmaILT, pSVpTKLT, pSV2LLT or pSV3LLT was introduced showed the LT gene expression. In every cultured cell, pSV3LLT showed higher expression of LT gene than pSV2LLT. In Table 1, 1 U of LT was defined as a concentration which can induce 50% lethality of the cell.

EXAMPLE 5

Production of LT in normal medium and in serum free medium

The medium of BHK-21 (C-13), wherein pSVeSmaILT, pSVpTKLT of pSV3LLT was introduced in Example 4, was renewed to MEM medium containing 10% bovine fetal serium, 25 μg/ml of mycophenolic acid and 250 μg/ml of xanthine and then the mycophenolic acid resistant cell was separated. The obtained mycophenolic acid resistant cell was grown on the whole base of 24-well multidish and was cultured on MEM medium containing 5% bovine fetal serum (FCS) or on MEM medium completely deficient in FCS for 24 hours. LT activity contained in the medium was measured. As shown in Table 2, the separated cell produced LT regardless of the serum.

TABLE 2

| | | LT (U/ml) culture medium | |
|---|---|---|---|
| Plasmid introduced | Transformant | 95% MEM 5% FCS | 100% MEM |
| pSVeSmaILT | E - 1 | 2048 | 512 |
| | E - 2 | 1024 | 256 |
| | E - 3 | 1024 | 256 |
| pSVpTKLT | TK - 1 | 512 | 512 |
| | TK - 2 | 1024 | 256 |
| | TK - 3 | 512 | 128 |
| pSV3LLT | L - 1 | 512 | 128 |
| | L - 2 | 1024 | 256 |
| | L - 3 | 256 | 128 |

EXAMPLE 6

Determination of base sequence of LT gene

Plasmid pLTB 4.2 was digested with the restriction enzyme BamHI and 4.2 Kb BamHI fragment was prepared by agarose gel electrophoresis. Plasmid pLTE 2.3 was digested with the restriction enzyme PstI or EcoRI-PstI to prepare 0.8 Kb PstI fragment or 1.2 Kb EcoRI-PstI fragment. The obtained three kinds of DNA fragment were digested with the restriction enzyme Sau3Ai, AluI, HaeIII, RsaI, AccI, HpaII or TaqI and the cleaved fragment was inserted at the BamHI, SmaI or AccI site of phage Ml3mpll (available from Pharmacia Japan), followed by the formation of the recombinant phage plaque employing E. coli JM 103 (available from Pharmacia Co., Ltd.) as the host. Single strand phage DNA was prepared from the separated recombinant phage. Determination of the base sequence was conducted by dideoxy method employing the obtained single strand DNA and synthesized DNA primer, ATGTTGCAGCACTGA (made by Takara Shuzo Co., Ltd.). The determined base sequence of LT

TABLE 1

| Plasmid introduced (8 μg/dish) | LT (U/ml) Established cell line | | | | |
|---|---|---|---|---|---|
| | CHO-K1 *(CCL-61) | L929 *(CCL-1) | Vero *(CCL-81) | BHK-21(C-13) *(CCL-10) | WI-26 VA4 *(CCL-95.1) |
| pSVeSmaILT | 64 | 4 | 16 | 128 | 16 |
| pSVpTKLT | 64 | 16 | 16 | 64 | 32 |
| pSV2LLT | 4 | 4 | 4 | 8 | 16 |
| pSV3LLT | 128 | 16 | 16 | 64 | 32 |
| pSVeSmaI | 0 | 0 | 0 | 0 | 0 |
| pSV2gpt | 0 | 0 | 0 | 0 | 0 |

(Note)
*(CCL: No. of American Type Culture Collection (ATCC))

gene and the amino acid sequence estimated from the
base sequence of exon was as follows:

```
AAGGGTGCAGAGATGTTATATATGATTGCTCTTCAGGGAACCGGCCTCCAGCTCACA
                                                        100
CCCCAGCTGCTCAACCGCCTCCTCTCTGAATTGACTGTCCCTTCTTTGGAACTCTAGGC
CTGACCCCACTCCCTGGCCCTCCCAGCCCACGATTCCCCTGACCCGACTCCCTTTCC
                    200
CAGAACTCAGTCGCCTGAACCCCCAGCCTGTGGTTCTCTCCTAGGCCTCAGCCTTTC
CTGCCTTTGACTGAAACAGCAGTATCTTCTACACGCTGGGGCTTCCCGCGGCCCAGC
             300
CCCGACCTAGAACCCGCCCGCTGCCTGCCACGCTGCCACTGCCGCTTCCTCTATAAA
                                                     400
GGGACCTGAGCGTCCGCGCGCAGGGGCTCCACACAGCAGGTGAGGCTCTCCTGCCCC
ATCTCCTTGGGCTGCCCGTGCTTCGTGCTTTGGACTACCGCCCCGAGTGTCCTGCCC
                                500
TCTGCCTGGGCCTCGGTCCCTCCTGCACCTGCTGCCTGGATCCCCGGCCTGCCTGGG
CCTGGGCCTTGGTGGGTTTGGTTTTGGTTTCCTTCTCTGTCTCTGACTCTCCATCTG
                        600
TCAGTCTCATTGTCTCTGTCACACATTCTCTGTTTCTGCCATGGTTCCTCTCTGTTC
CCTTCCTGTCTCTCTCTGTCTCCCTCTGCTCACCTTGGGGTTTCTCTGACTGCATCT
                700
TGTCCCCTTCTCTGTCCGATCTCTCTCTCGGGGGTCGGGGGGTGCTGTCTCCCAGGG
                                                         800
CGGGAGGTCTGTCTTCCGCCGCGTGCCCCGCCCCGCTCACTGTCTCTCTCTCTCT
CTCTTTCTCTGCAGGTTCTCCCC ATG ACA CCA CCT GAA CGT CTC TTC
                        met thr pro pro glu arg leu phe
                                                    -30
CTC CCA AGG GTG TGT GGC ACC ACC CTA CAC CTC CTC CTT CTG
leu pro arg val cys gly thr thr leu his leu leu leu leu
                                    -20
        900
GGG CTG CTG CTG GTT CTG CTG CCT GGG GCC CAG GTGAGGCAGCAGG
gly leu leu leu val leu leu pro gly ala gln
                                    -10
AGAATGGGGGCTGCTGGGGTGGCTCAGCCAAACCTTGAGCCCTAGAGCCCCCCTCAA
        1000
CTCTGTTCTCCTAG GGG CTC CCT GGT GTT GGC CTC ACA CCT TCA
               gly Leu Pro Gly Val Gly Leu Thr Pro Ser
                 1
GCT GCC CAG ACT GCC CGT CAG CAC CCC AAG ATG CAT CTT GCC
Ala Ala Gln Thr Ala Ag  Gln His Pro Lys Met His Leu Ala
 10                                     20
                  1100
CAC AGC AAC CTC AAA CCT GCT GCT CAC CTC ATT G GTAAACATCCA
His Ser Asn Leu Lys Pro Ala Ala His Leu Ile G
                              30
CCTGACCTCCCAGACATGTCCCCACCAGCTCTCCTCCTACCCCTGCCTCAGGAACCC
              1200
AAGCATCCACCCCTCTCCCCCAACTTCCCCCACGCTAAAAAAAAACAGAGGGAGCCCA
CTCCTATGCCTCCCCCTGCCATCCCCCAGGAACTCAGTTGTTCAGTGCCCACTTCCT
       1300
CAGGGATTGAGACCTCTGATCCAGACCCCTGATCTCCCACCCCCATCCCCTATGGCT
CTTCCTAG GA GAC CCC AGC AAG CAG AAC TCA CTG CTC TGG AGA
         ly Asp Pro Ser Lys Gln Asn Ser Leu Leu Trp Arg
                                          40
       1400
GCA AAC ACG GAC CGT GCC TTC CTC CAG GAT GGT TTC TCC TTG
Ala Asn Thr Asp Arg Ala Phe Leu Gln Asp Gly Phe Ser Leu
          50                                       60
AGC AAC AAT TCT CTC CTG GTC CCC ACC AGT GGC ATC TAC TTC
Ser Asn Asn Ser Leu Leu Val Pro Thr Ser Gly Ile Tyr Phe
                              70
              1500
GTC TAC TCC CAG GTG GTC TTC TCT GGG AAA GCC TAC TCT CCC
Val Tyr Ser Gln Val Val Phe Ser Gly Lys Ala Tyr Ser Pro
                      80
AAG GCC ACC TCC TCC CCA CTC TAC CTG GCC CAT GAG GTC CAG
Lys Ala Thr Ser Ser Pro Leu Tyr Leu Ala His Glu Val Gln
    90                                      100
                                       1600
CTC TTC TCC TCC CAG TAC CCC TTC CAT GTG CCT CTC CTC AGC
Leu Phe Ser Ser Gln Tyr Pro Phe His Val Pro Leu Leu Ser
                              110
TCC CAG AAG ATG GTG TAT CCA GGG CTG CAG GAA CCC TGG CTG
Ser Gln Lys Met Val Tyr Pro Gly Leu Gln Glu Pro Trp Leu
                 120                                130
CAC TCG ATG TAC CAC GGG GCT GCG TTC CAG CTC ACC CAG GGA
His Ser Met Tyr His Gly Ala Ala Phe Gln Leu Thr Gln Gly
                                  140
```

```
                                    1700
GAC CAG CTA TCC ACC CAC ACA GAT GGC ATC CCC CAC CTA GTC
Asp Gln Leu Ser Thr His Thr Asp Gly Ile Pro His Leu Val
                    150
CTC AGC CCT AGT ACT GTC TTC TTT GGA GCC TTC GCT CTG TAG
Leu Ser Pro Ser Thr Val Phe Phe Gly Ala Phe Ala Leu stop
160                                     170
                      1800
AACTTGGAAAAATCCAGAAAGAAAAAATAATTGATTTCAAGACCTTCTCCCCATTCT
GCCTCCATTCTGACCATTTCAGGGGTCGTCACCACCTCTCCTTTGGCCATTCCAACA
        1900
GCTCAAGTCTTCCCTGATCAAGTCACCGGAGCTTTCAAAGAAGGAATTCTAGGCATC
                                                        2000
CCAGGGGACCCACACCTCCCTGAACCATCCCTGATGTCTGTCTGGCTGAGGATTTCA
AGCCTGCCTAGGAATTCCCAGCCCAAAGCTGTTGGTCTTGTCCCACCAGCTAGGTGG
                                2100
GGCCTAGATCCACACACAGAGGAAGAGCAGGCACATGGAGGAGCTTGGGGGATGACT
AGAGGCAGGGAGGGGACTATTTATGAAGGCAAAAAAATTAAATTATTTATTTATGGA
                    2200
GGATGGAGAGAGGGGAATAATAGAAGAACATCCAAGGAGAAACAGAGACAGGCCCAA
GAGATGAAGAGTGAGAGGGCATGCGCACAAGGCTGACCAAGAGAGAAAGAAGTAGGC
        2300
ATGAGGGATCACAGGGCCCCAGAAGGCAGGGAAAGGCTCTGAAAGCCAGCTGCCGAC
CAGAGCCCCACACGGAGGCATCTGCACCCTCGATGAAGCCCAATAAACCTCTTTTCT
2400
  CTGAAATGCTGTCTGCTTGTGTGTGTGTGTCTGGGAGTGAGAACTTCCCAGTCTATC
                                            2500
TAAGGAATGGAGGGAGGGACAGAGGGCTCAAAGGGACGAAGAGCTGTGGGGAGAACA
AAAGGATAAGGGCTCGAGAGAGCTTCAGGGATATGTGATGGATCACCAGGTGAGGCC
                    2600
GCCAGACTGCTGCAGGGGAAGCAAAGGAGAAGCTGAGAAGATGAAGGAAAAGTCAGG
GTCTGGAGGGGCGGGGGTCAGGGAGCT
```

LT gene consists of at least four exons and three introns. 1st Exon includes TATAbox-like sequence (TATAAA) which is normally found in the eucaryote promoter region. 2nd Exon includes initiation codon (ATG) and 4th exon includes termination codon (TAG) and polyadenylation signal. In known LT cDNA [Gray, P. W. et al. (1984), Nature, Vol. 312, P712], bases are deleted which correspond to 478th C, 1959th C, 2044th C and 2186th G of the base sequence shown as above, respectively. It was also found that the base sequence of GAGGTTTAT present at the 5' terminal of known cDNA was not present in the base sequence of LT gene. Further, it was found that the codon corresponding to 26th amino acid of known LT polypeptide is ACC, which codes threonine (THr), whereas in LT gene the corresponding codon is AAC, which codes asparagine (Asn).

EXAMPLE 7

Selection of LT resistant cell

BHK-21 (C-13) [ATCC CCL 10], CHO-K1 [ATCC CCL-61], FL [ATCC CCL 62], WISH [ATCC CCL 25], Vero [ATCC CCL 81] and WI-26 VA4 [ATCC CCL 95.1] were cultured on the whole base of 24-well multidish plate. After replacing the medium with MEM medium containing 2000 U/ml of LT and 5% FCS, the cells were cultured for 48 hours. Any morphological change was not observed in BHK-21 (C-13), Vero and WI-26 VA4. However, it was observed that CHO-K1, FL and WISH were deformed and peeled off from the base of the culture vessel. From the result, BHK-21 (C-13), Vero and WI-26 VA4 were selected as the cell resistant to 2000 U/ml of LT.

The above six kinds of cell and CHO dhfr⁻ [Urlaub, G. and Chasin, L. (1980), Pro. Natl. Acad. Sci. USA, Vol. 77, P4216] were cultured on the whole base of 24-well multiwell plate. After replacing the medium with nucleoside-containing MEM α medium (made by GIBCO, Co., Ltd.) containing 100 U/ml of LT, 1 μg/ml of Actinomycin D and 5% FCS, the cells were cultured for 24 hours. Any morphological change was not observed in BHK-21 (C-13), Vero and WI-26 VA4. However, the other cells were deformed and peeled off from the base of the culture vessel.

EXAMPLE 8

Collection of LT resistant cell

CHO dhfr⁻ was cultured on the whole base of a flask having 75 cm² of base area. After replacing the medium with nucleoside-containing MEM α medium (made by GIBCO Co., Ltd.) containing 250 U/ml of LT, 0.1 μg/ml of Actinomycin D and 5% FCS, the cell was cultured for 24 hours. The medium was then renewed to the medium deficient in Actinomycin D and the culture was continued further for about 3 weeks. CHO dhfr⁻ 2-3 was separated from the formed colony. CHO dhfr⁻ 2-3 had the LT resistance to not less than 1000 U/ml of LT.

CHO dhfr⁻ was cultured on the whole base of a flask having 25 cm² of base area. After replacing the medium with nucleoside-containing MEM α medium containing 1000 U/ml of LT and 5% FCS, the cell was cultured for about one month. CHO dhfr⁻6 was separated, which had the LT resistance to not less than 1000 U/ml of LT.

EXAMPLE 9

Preparation of pSVeLTdhfr and pSVLpTKdhfr

Figure 8:
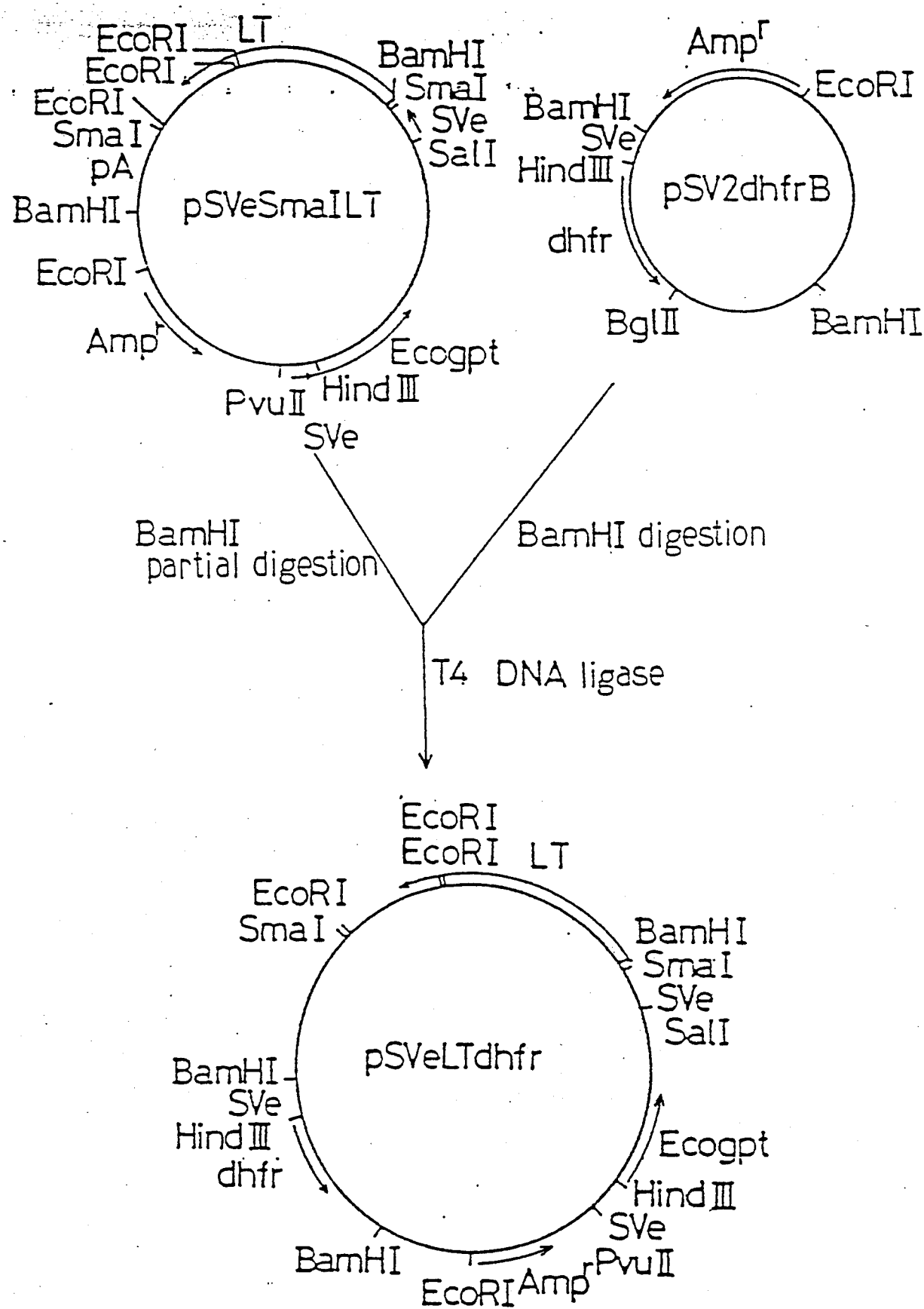
FIG. 8 shows construction of plasmid pSVeLTdhfr.

LT expression vector pSVeLTdhfr was prepared according to the procedure shown in FIG. 8. Plasmid pSV2dhfrB was prepared by converting the HindIII site of pSV2dhfr [Subramani, S. et al. (1981), Molecular and Cellular Biology, Vol. 1, P854] into BamHI by means of BamHI linker.

BamHI fragment of about 1.9 Kb containing dhfr from pSV2dhfrB was inserted into the BamHI site of pSVeSmaILT, which was partially digested with BamHI, to prepare pSVeLTdhfr.

Figure 9A:
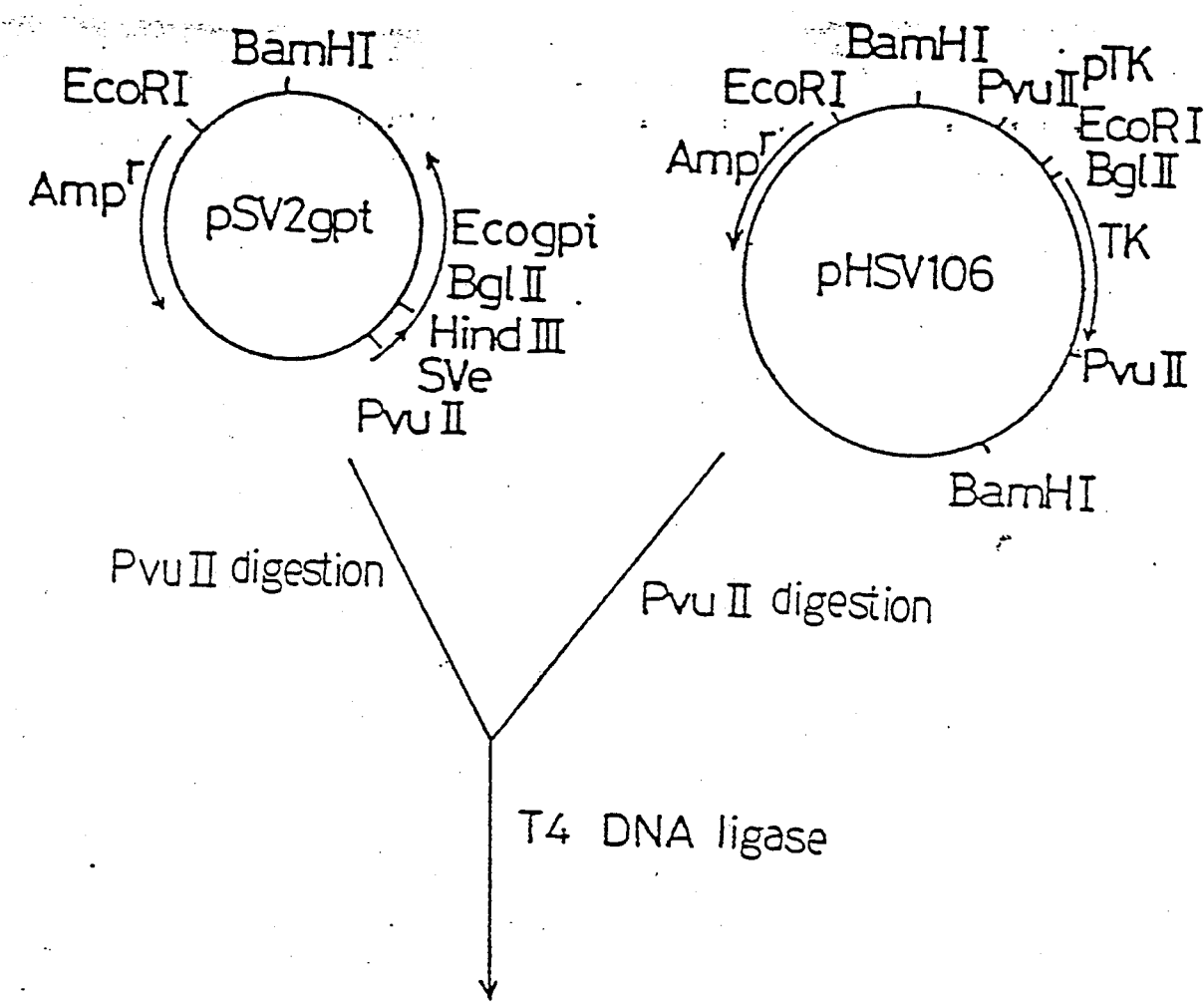
FIG. 9(a) shows construction of plasmid pSVLpTK.
Figure 9A:
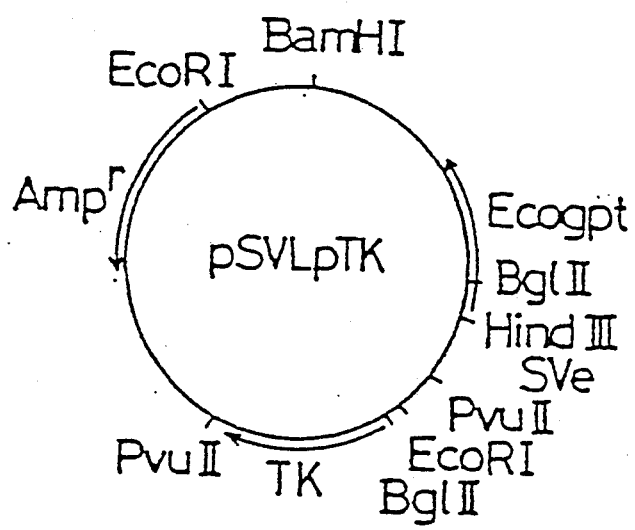
Figure 9:
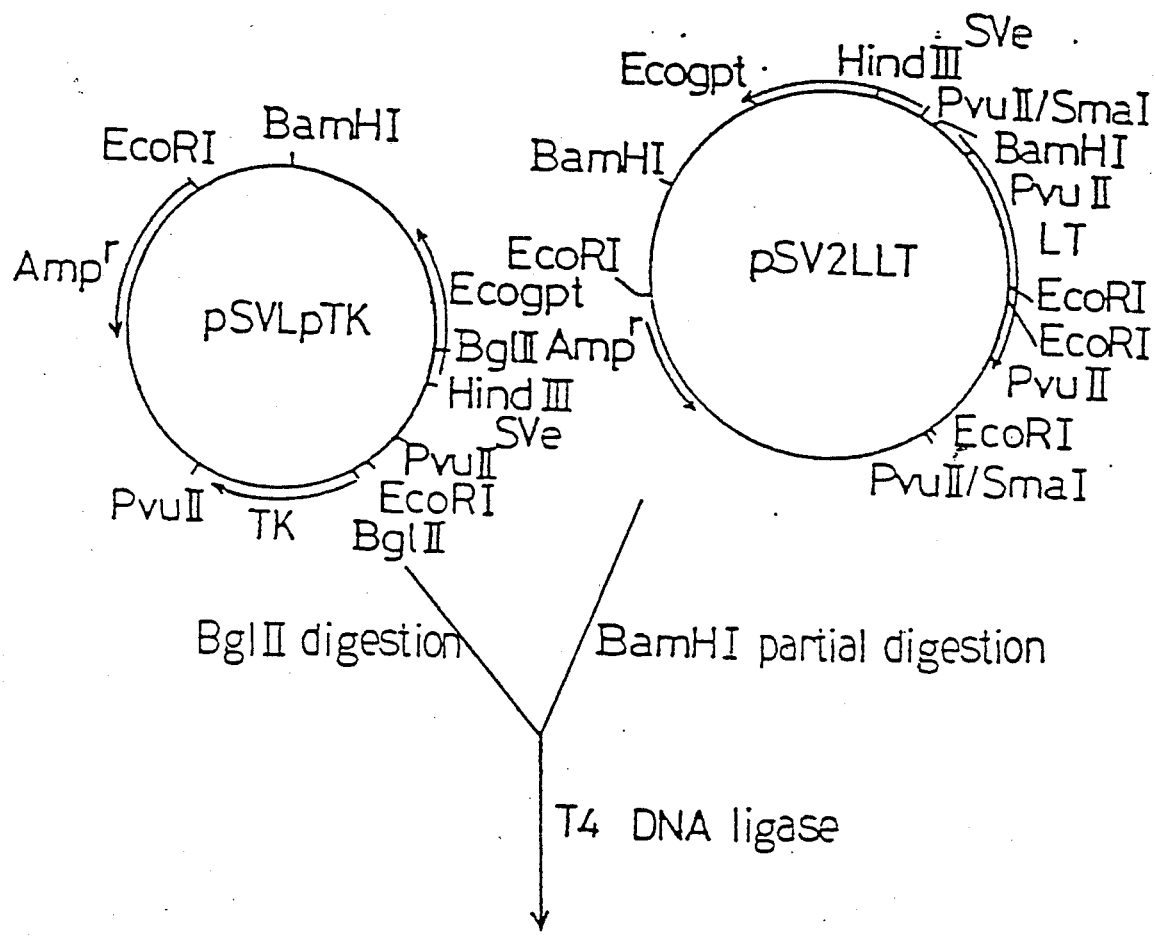
Figure 9:
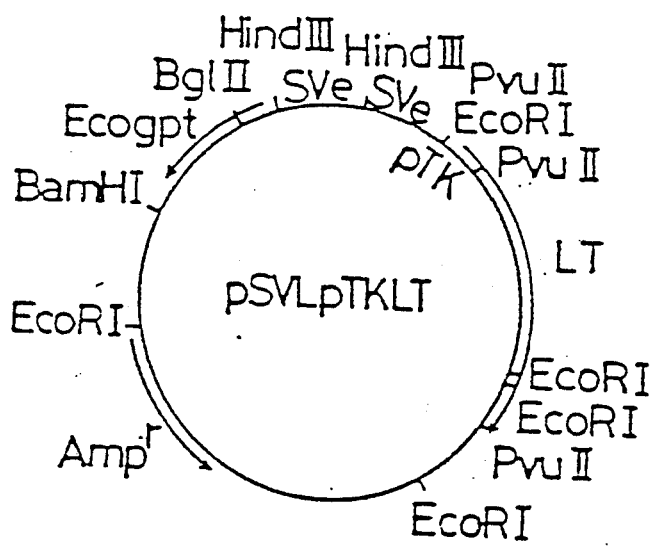
Figure 9C:
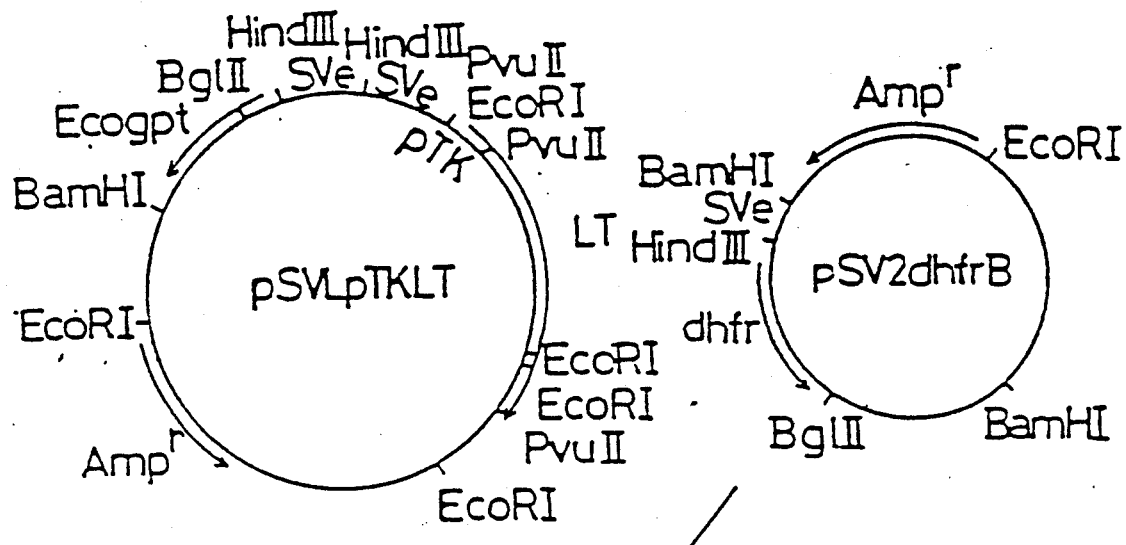
FIG. 9(c) shows construction of plasmid pSVLpTKLTdhfr.
Figure 9C:
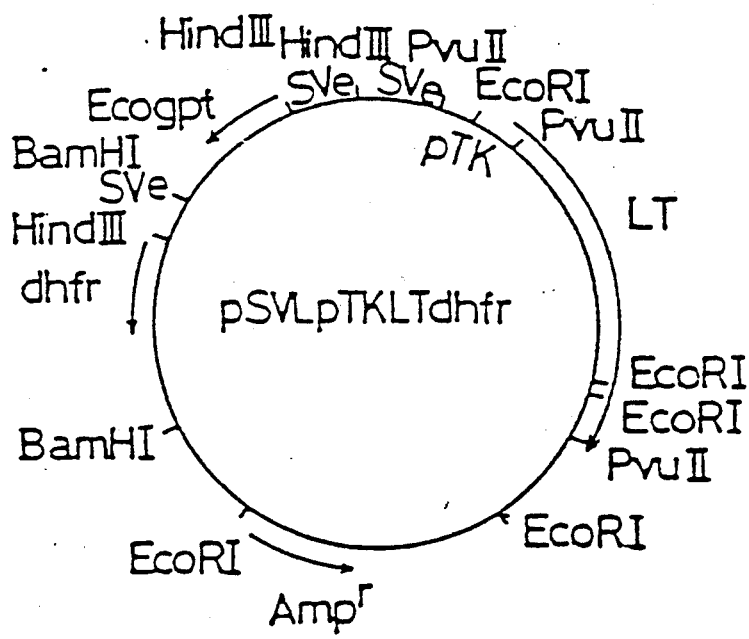

LT expression vector pSVLpTKdhfr was prepared according to the procedure shown in FIGS. 9(a), 9(b) and 9(c). PvuII fragment containing thymidin kinase gene of pHSV 106 [McKnight, S. L. and Gabis, E. R. (1980), Nucleic Acids Res., Vol. 8, P5931: available from Bethesda Research Laboratory] was inserted into the PvuII site of pSV2gpt [ATCC 37145: Mulligan, R. C. and Berg, P. (1980), Science, Vol. 209, P1422] to prepare pSVLpTK [FIG. 9(a)]. BglII fragment containing SV40 promoter and thymidine kinase promoter from pSVLpTK was inserted into the BamHI site of pSV2LLT, which was partially digested with BamHI, to prepare pSVLpTKLT [FIG. 9(b)]. Finally, BamHI fragment containing dhfr gene from pSV2dhfrB was inserted into the BamHI site of pSVLpTKLT to prepare pSVLpTKLTdhfr [FIG. 9(c)].

EXAMPLE 10

Transformation of LT resistant cell with LT expression vector

Employing the LT expression vector pSVeLTdhfr or pSVLpTKLTdhfr, transformation was conducted on BHK-21 (C-13), CHO-K1, FL, WISH, Vero, WI-26 VA4, CHO dhfr$^-$, CHO dhfr$^-$ 2-3 and CHO dhfr$^-$ 6 as the hose according to Wigler et al. [Wigler et al. (1977), Cell, Vol. 11, P223].

Coprecipitate of plasmid-calcium phosphate was added to the cell ($2 \times 10^5$ cells/3 ml medium/culture dish of 6 cm diameter) which was previously cultured on the medium containing 5% FCS. The medium was renewed after 18 hours and the cell was cultured for 48 hours. The medium of CHO dhfr$^-$, CHO dhfr$^-$ 2-3 and CHO dhfr$^-$ 6 was replaced with nucleoside-deficient MEM α medium (made by GIBCO Co., Ltd.) containing 5% FCS, 25 μg/ml of mycophenolic acid and 250 μg/ml of xanthine. The medium of the other cells was replaced with MEM medium containing 5% FCS, 25 μg/ml of mycophenolic acid, 250 μg/ml of xanthine, 25 μg/ml of adenine, 5 μg/ml of thymidine and 0.1 μg/ml of aminopterin. After culturing the cell for about 3 weeks, the formed colony was isolated and grown on 24-well multidish plate. The medium was renewed to that containing or not containing 5% FCS and, after cultivation for 48 hours, an amount of LT contained in the medium was measured by the cellular lethal effect of LT employing L929 cell as the target cell [Ruff, M. R. and Gifford, G. E. (1981), Lymphokines, Vol. 2, P235], i.e. the cell was cultured in 96-well multidish at $2 \times 10^4$ cells/well/10 μl medium for a day, to which, after the culture medium was removed, 100 μl of samples diluted to various concentrations with Eagle's MEM medium containing 1 μg/ml of Actinomycin D and 5% FCS were added. After 20 hours, cellular degeneration and lethal effect of LT was measured.

As shown in Tables 3 to 7, transformant which shows LT productivity of more than 500 U/ml was obtained from BHK-21 (C-13), Vero, WI-26 VA4, CHO dhfr$^-$ 2-3 and CHO dhfr$^-$ 6 when the LT expression vector was introduced into these cells. However, such transformant could not be obtained from CHO-K1, FL, WISH and CHO dhfr$^-$. In Tables 3 to 7, three typical transformants having high LT productivity are shown.

TABLE 3

LT production by the transformed BHK-21 (C-13)

| Plasmid introduced | Transformant | LT (U/ml) culture medium 95% MEM 5% FCS | 100% MEM |
|---|---|---|---|
| pSVeLTdhfr | BE - 1 | 1300 | 400 |
| | BE - 2 | 1300 | 500 |
| | BE - 3 | 1100 | 400 |
| pSVLpTKLTdhfr | BTK - 1 | 1600 | 500 |
| | BTK - 2 | 1500 | 300 |
| | BTK - 3 | 1100 | 300 |

TABLE 4

LT production by the transformed Vero

| Plasmid introduced | Transformant | LT (U/ml) culture medium 95% MEM 5% FCS | 100% MEM |
|---|---|---|---|
| pSVeLTdhfr | VE - 1 | 700 | 200 |
| | VE - 2 | 500 | 100 |
| | VE - 3 | 500 | 200 |
| pSVLpTKLTdhfr | VTK - 1 | 1000 | 300 |
| | VTK - 2 | 900 | 200 |
| | VTK - 3 | 800 | 200 |

TABLE 5

LT production by the transformed WI-26 VA4

| Plasmid introduced | Transformant | LT (U/ml) culture medium 95% MEM 5% FCS | 100% MEM |
|---|---|---|---|
| pSVeLTdhfr | WE - 1 | 400 | 100 |
| | WE - 2 | 400 | 100 |
| | WE - 3 | 300 | 100 |
| pSVLpTKLTdhfr | WTK - 1 | 600 | 200 |
| | WTK - 2 | 400 | 100 |
| | WTK - 3 | 400 | 100 |

TABLE 6

LT production by the transformed CHO dhfr$^-$ 2-3

| Plasmid introduced | Transformant | LT (U/ml) culture medium 95% α-MEM (not containing nucleoside) 5% FCS | 100% α-MEM (not containing nucleoside) |
|---|---|---|---|
| pSVeLTdhfr | 2 - 3E - 1 | 1,200 | 300 |
| | 2 - 3E - 2 | 1,200 | 300 |
| | 2 - 3E - 3 | 1,000 | 300 |
| pSVLpTKLTdhfr | 2 - 3TK - 1 | 1,800 | 500 |
| | 2 - 3TK - 2 | 1,000 | 200 |
| | 2 - 3TK - 3 | 1,000 | 200 |

TABLE 7

LT production by the transformed CHO dhfr$^-$ 6

| Plasmid introduced | Transformant | LT (U/ml) culture medium 95% -MEM (not containing nucleoside) 5% FCS | 100% -MEM (not containing nucleoside) |
|---|---|---|---|
| psVeLTdhfr | 6E - 1 | 1,100 | 300 |
| | 6E - 2 | 1,000 | 300 |
| | 6E - 3 | 1,000 | 200 |
| pSVLpTKLTdhfr | 6TK - 1 | 1,500 | 400 |
| | 6TK - 2 | 1,100 | 300 |

TABLE 7-continued

LT production by the transformed CHO dhfr⁻ 6

| Plasmid introduced | Transformant | LT (U/ml) culture medium | |
|---|---|---|---|
| | | 95% -MEM (not containing nucleoside) 5% FCS | 100% -MEM (not containing nucleoside) |
| | 6TK - 3 | 1,000 | 300 |

EXAMPLE 11

Selection of Transformant by Methotrexate (Mtx)

$10^3$ to $3 \times 10^5$ Cells of the BHK transformant obtained in Example 10 were planted on a dish of 10 cm diameter. After cultivation on the medium containing 50 nM to 500 nM of Mtx for about one month, the colonies resistant to each concentration of Mtx were isolated. The cells were grown on 24-well multidish plate and then the medium was renewed to that containing or not containing 5% FCS. After 48 hours, an amount of LT contained in the medium was measured. As shown in Table 8, the cell showing higher LT productivity than the mother cell was obtained from the cell selected by 100 nM and 200 nM of Mtx.

TABLE 8

| Mother cell | Mtx concentration for selection (nM) | Selected cell | LT (U/ml) culture medium | |
|---|---|---|---|---|
| | | | + FCS | − FCS |
| BE-2 | 100 | BE-2-1 | 8,000 | 4,000 |
| | 100 | BE-2-2 | 5,500 | 5,000 |
| | 200 | BE-2-3 | 5,000 | 2,000 |
| BTK-1 | 200 | BTK-1-1 | 15,000 | 3,500 |
| | 200 | BTK-1-2 | 10,000 | 3,000 |
| | 100 | BTK-1-3 | 10,000 | 3,000 |

Each $10^3$ to $3 \times 10^5$ cells of the CHO dhfr⁻ 2-3 and CHO dhfr⁻ 6 transformants obtained in Example 10 were planted on a dish of 10 cm diameter. After cultivation on the medium containing 1 nM to 1000 nM of Mtx for about one month, the colonies resistant to each concentration of Mtx were isolated. The cells were grown on 24 hole multiwell plate and then the medium was renewed to that containing or not containing 5% FCS. After 48, hours, an amount of LT contained in the medium was measured. As shown in Table 9, the cell showing higher LT productivity than the mother cell was obtained from the cell selected by every concentration of LT.

TABLE 9

| Mother cell | Mtx concentration for selection (nM) | Selected cell | LT (U/ml) culture medium | |
|---|---|---|---|---|
| | | | + FCS | − FCS |
| 2-3E-1 | 1 | 2-3E-1-0 | 3,000 | 500 |
| | 20 | 2-3E-1-1 | 13,500 | 8,000 |
| | 50 | 2-3E-1-8 | 30,000 | 8,000 |
| | 50 | 2-3E-1-9 | 20,000 | 8,000 |
| | 200 | 2-3E-1-55 | 35,000 | 10,000 |
| | 200 | 2-3E-1-56 | 35,000 | 10,000 |
| | 500 | 2-3E-1-76 | 35,000 | 12,000 |
| | 500 | 2-3E-1-77 | 30,000 | 12,000 |
| | 1,000 | 2-3E-1-80 | 28,000 | 10,000 |
| 6TK-1 | 50 | 6TK-1-1 | 40,000 | 10,000 |
| | 50 | 6TK-1-2 | 40,000 | 20,000 |
| | 50 | 6TK-1-3 | 35,000 | 18,000 |
| | 100 | 6TK-1-101 | 53,000 | 10,000 |

TABLE 9-continued

| Mother cell | Mtx concentration for selection (nM) | Selected cell | LT (U/ml) culture medium | |
|---|---|---|---|---|
| | | | + FCS | − FCS |
| | 100 | 6TK-1-102 | 50,000 | 10,000 |
| | 100 | 6TK-1-103 | 30,000 | 10,000 |

EXAMPLE 12

Collection of LT

The LT-producing cell 2-3E-1-55 obtained in Example 11 was cultured on the MEM α medium (made by GIBCO Co., Ltd.) containing 5% FCS. After dialysis of 100 ml of the culture medium against 5 nM phosphate buffer solution, LT was adsorbed on DEAE-cellulose column ($2 \times 10$ cm) and eluted with 0 to 3.0 M gradient of NaCl. The yield was about 75% and $8.6 \times 10^5$ U of LT was collected.

EXAMPLE 13

Preparation of pLT-R1, pLT-R2, pLT-R3 and pLT-R3dhfr

LT expression vectors pLT-R1, pLT-R2, pLT-R3 and pLT-R3dhfr were prepared according to the following steps (1) and (2).

Figure 10:
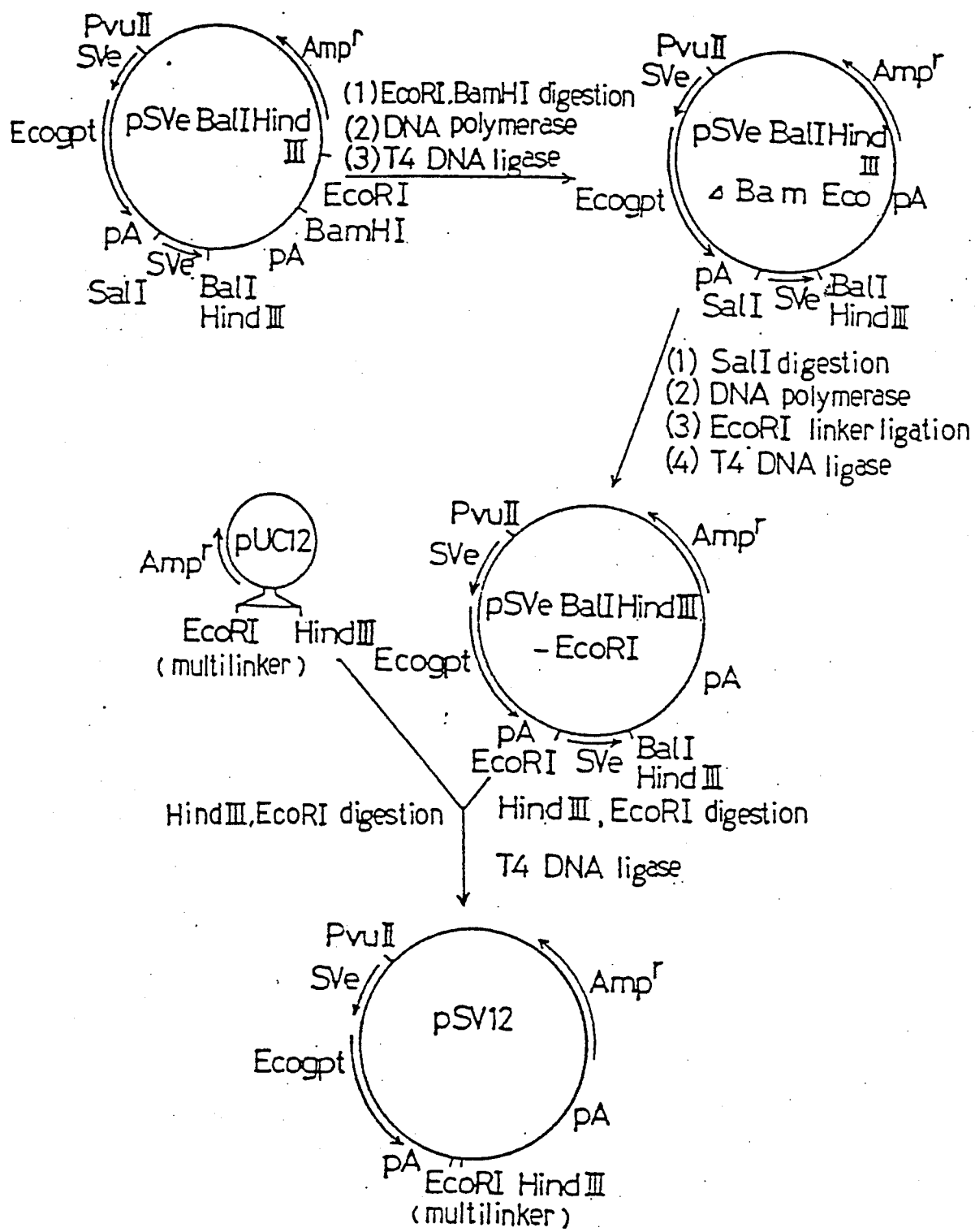
FIG. 10 shows construction of plasmid pSV12.

(1) Preparation of pLT pSV12 were prepared according to the procedure shown in FIG. 10. Plasmid pSVeBalIHindIII, which has been described in detail in Japanese Patent Application No. 152810/1985, was digested with EcoRI and BamHI. The cleavage sites were repaired with DNA polymerase and ligated with T4 DNA ligase to prepare pSVeBAlIHindIII BamEco. The SalI site of pSVeBalI-HindIII BamEco was then converted into EcoRI site by means of EcoRI linker (GGAATTCC) to prepare pSVeBalIHindIII-EcoRI. Finally, EcoRI-HindIII fragment containing multicloning site of pUC12 was inserted into the EcoRI-HindIII site of pSVeBalIHindIII-EcoRI to prepare pSV12.

Figure 11:
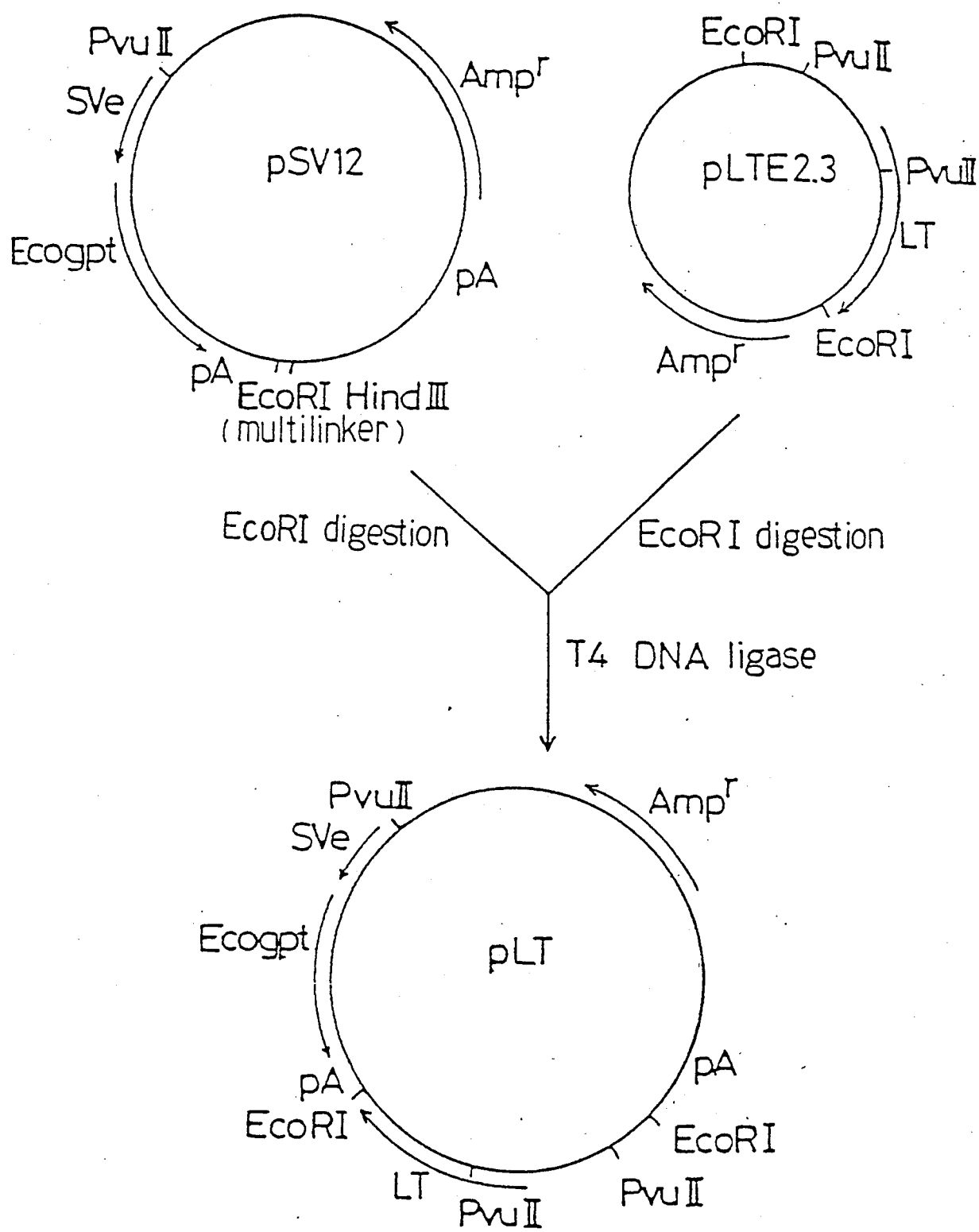
FIG. 11 shows construction of plasmid pLT.

Plasmid pLT was prepared according to the procedure shown in FIG. 11. EcoRI 2.3 Kb fragment containing LT gene from pLTE 2.3 was inserted into the EcoRI site of pSV12 to prepare pLT.

(2) Preparation of the expression vectors pLT-R1, pLT-R2, pLT-R3 and pLT-R3dhfr

Figure 12:
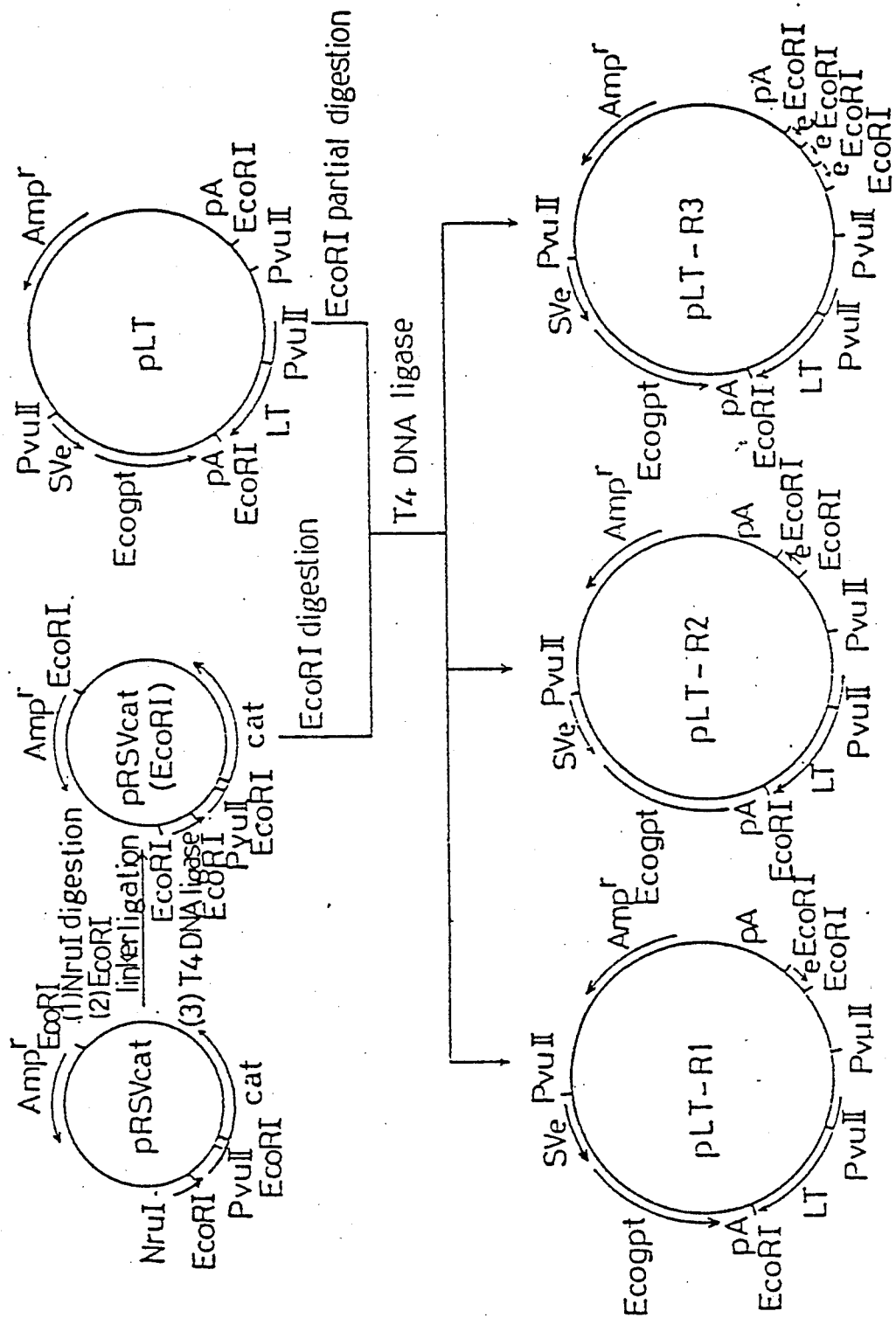
FIG. 12 shows construction of plasmids pLT-R1, pLT-R2 and pLT-R3.

Plasmids pLT-R1, pLT-R2 and pLT-R3 were prepared according to the procedure shown in FIG. 12. NruI site of pRSVcat (available from ATCC, ATCC 37152) was converted to EcoRI site by means of EcoRI linker (GGAATTCC) to prepare pRSVcat (EcoRI). After digestion of pRSVcat (EcoRI) with EcoRI, the EcoRI fragment of about 300 bp containing the RSV enhancer sequence was inserted into the EcoRI site of pLT, which was partially digested with EcoRI, to prepare pLT-R1, pLT-R2 and pLT-R3.

Figure 13:
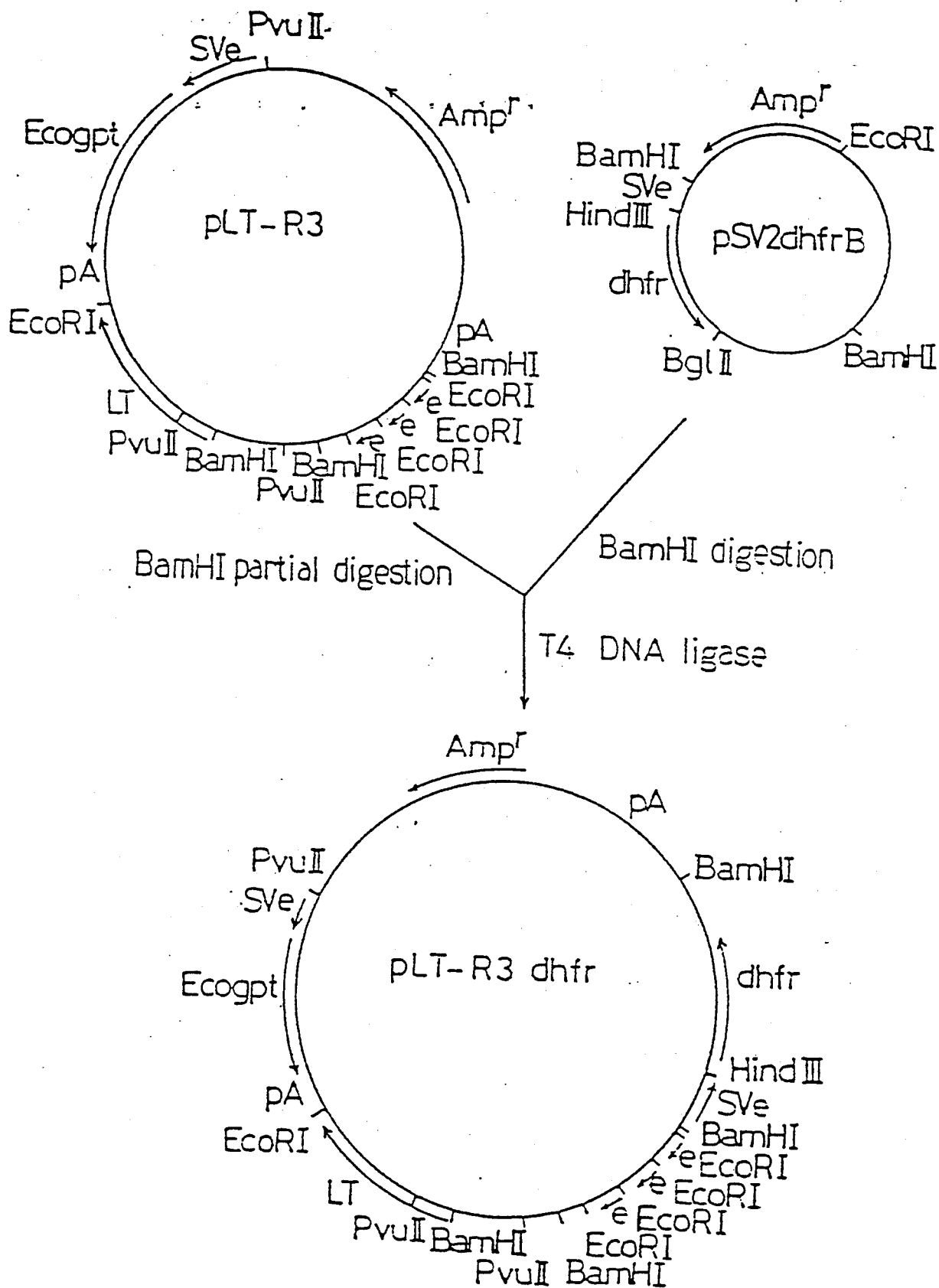
FIG. 13 shows construction of plasmid pLT-R3dhfr.

The pLT-R3dhfr was prepared according to the procedure shown in FIG. 13. Plasmid pSV2dhfrB, which was prepared by converting the PvuII site of pSV2dhfr (ATCC 37145) to BamHI site by means of BamHI linker, was digested with BamHI. The obtained BamHI fragment containing dihydrofolate reductase gene was inserted into the BamHI site of pLT-R3, which was partially digested with BamHI, to prepare pLT-R3dhfr.

EXAMPLE 14

Introduction of LT expression vector into cultured animal cell and production of LT Employing the LT expression vector pLT-R1, pLT-R2, pLT-R3 or pLT-R3dhfr, transformation was conducted on BHK-21 (C-13) as the hose according to Wigler et al. [Wigler et al. (1977), Cell, Vol. 11, P223].

Coprecipitate of plasmid-calcium phosphate was added to the cell ($2 \times 10^5$ cells/3 ml medium/culture dish of 6 cm diameter) which was previously cultured on the medium containing 5% FCS. The medium was renewed after 4 hours. After 48-hour cultivation, an amount of LT contained in the medium was measured by the cellular lethal effect of LT employing L292 cell as the target cell [Ruff, M. R. and Gifford, G. E. (1981), Lymphokines, Vol. 2, P235], i.e. the cell was cultured in 96-well multidish at $2 \times 10^4$ cells/well/100 μl medium for a day, to which, after the culture medium was removed, 100 μl of samples diluted to various concentrations with Eagle's MEM medium containing 1 μg/ml of Actinomycin D and 5% fetal calf serium were added. After 20 hours, cellular degeneration and lethal effect of LT was measured.

As shown in Table 10, introduction of the vector having the RSV enhancer sequence produced higher amount of LT than that of the vector not having the RSV enhancer sequence.

TABLE 10

| Introduced vector | LT (U/ml) |
|---|---|
| pLT | 3 |
| pLT-R1 | 16 |
| pLT-R2 | 7 |
| pLT-R3 | 105 |
| pLT-R3dhfr | 100 |

The medium of BHK-21 (C-13) wherein pLT-R3 or pLT-R3dhfr was introduced was replaced with MEM medium containing 5% FCS, 25 μg/ml of mycophenolic acid, 250 μg/ml of xanthine and 0.1 μg/ml of aminopterine, followed by cultivation for about 3 weeks. The formed colonies were isolated and the cells were grown on 24-well multidish plate. After 72 hours, an amount of LT contained in the medium was measured. As shown in Table 11, the isolated transformant produced LT.

TABLE 11

| Introduced vecter | Transformant | LT (U/ml) |
|---|---|---|
| pLT - R3 | BLT - 1 | 1,200 |
|  | BLT - 2 | 1,600 |
|  | BLT - 3 | 1,500 |
|  | BLT - 4 | 1,000 |
|  | BLT - 5 | 1,100 |
| pLT - R3dhfr | BLTD - 1 | 1,200 |
|  | BLTD - 2 | 1,500 |
|  | BLTD - 3 | 1,300 |
|  | BLTD - 4 | 1,100 |
|  | BLTD - 5 | 1,100 |

Table 11 shows the results of five typical LT-producing cells among the isolated transformants.

EXAMPLE 15

Selection of transformant by methotrexate (Mtx)

$10^3$ to $3 \times 10^5$ Cells of the transformant with pLT-R3dhfr obtained in Example 14 were plated on a dish of 10 cm diameter. After cultivation on the medium containing 1 nM, 50 nM, 150 nM or 500 nM or Mtx for about one month, the colonies resistant to each concentration of Mtx were isolated. The cells were grown on 24-well multidish plate and the medium was renewed to that containing or not containing 5% FCS. After 72 hours, an amount of LT contained in the medium was measured. As shown in Table 12, the cell showing higher LT productivity than the mother cell was obtained from the cell selected by Mtx.

TABLE 12

| Mother cell | Mtx concentration for selection (nM) | Selected cell | LT (U/ml) culture medium 95% MEM 5% FCS | 100% MEM |
|---|---|---|---|---|
| BLTD-1 | 1 | BLTD-1-1 | 2,200 | 1,800 |
|  | 100 | BLTD-1-2 | 4,500 | 3,000 |
|  | 100 | BLTD-1-3 | 5,000 | 2,500 |
|  | 200 | BLTD-1-4 | 7,000 | 4,000 |
|  | 200 | BLTD-1-5 | 8,500 | 5,000 |
| BLTD-4 | 1 | BLTD-4-1 | 3,000 | 1,800 |
|  | 100 | BLTD-4-2 | 5,500 | 2,500 |
|  | 100 | BLTD-4-3 | 5,000 | 3,000 |
|  | 200 | BLTD-4-4 | 10,000 | 7,500 |
|  | 200 | BLTD-4-5 | 8,000 | 5,000 |

What we claim is:

1. A recombinant DNA sequence which codes for human lymphotoxin and contains the genomic DNA sequence for lymphotoxin, including introns.

2. A lymphotoxin expression vector comprising a DNA sequence containing the genomic DNA sequence, including introns, for human lymphotoxin operably linked to a promoter selected from the group consisting of an early promoter of SV40, a thymidine kinase promoter of herpes simplex virus and a late promoter of SV40.

3. A lymphotoxin expression vector according to claim 2, wherein said vector is a plasmid selected from the group consisting of pSVeSmaILT, pSVpTKLT, pSV2LLT and pSV3LLT.

4. A lymphotoxin expression vector according to claim 2, wherein said vector is a plasmid pSVeLTdhfr or pSVLpTKLTdhfr, said plasmid having an amplifiable dihydrofolate reductase gene.

5. A lymphotoxin expression vector comprising a DNA sequence wherein a DNA sequence containing the genomic DNA sequence, including introns, for human lymphotoxin operably linked to the human lymphotoxin promoter region, and an enhancer sequence of Rous sarcoma virus which activates said promoter.

6. A lymphotoxin expression vector according to claim 5, wherein said vector is a plasmid selected from the group consisting of pLT-R1, pLT-R2 and pLT-R3.

7. A lymphotoxin expression vector according to claim 5, wherein said vector is a plasmid pLT-R3dhfr which has an amplifiable dihydrofolate reductase gene.

* * * * *

UNITED STATES PATENT AND TRADEMARK OFFICE
CERTIFICATE OF CORRECTION

PATENT NO.   : 4,988,624

DATED        : January 29, 1991

INVENTOR(S)  : KAKUTANI et al

It is certified that error appears in the above-identified patent and that said Letters Patent is hereby corrected as shown below:

On the cover page, Item [75] Inventors, change "yasuhiro" to --Yasuhiro--.

On the cover page, after Item [22], the following should appear:

--[30]          Foreign Application Priority Data

| Jul. 3, 1985  | [JP] | Japan | .......................... | 60-147371 |
| Oct. 15, 1985 | [JP] | Japan | .......................... | 60-230744 |
| Feb. 5, 1986  | [JP] | Japan | .......................... | 61-23637  |
| Feb. 19, 1986 | [JP] | Japan | .......................... | 61-34962--.|

Signed and Sealed this

Eighth Day of November, 1994

*Attest:*

BRUCE LEHMAN

*Attesting Officer*   *Commissioner of Patents and Trademarks*